(12) United States Patent
Cong et al.

(10) Patent No.: US 7,255,474 B2
(45) Date of Patent: Aug. 14, 2007

(54) PARALLEL INFRARED SPECTROSCOPY APPARATUS AND METHOD

(75) Inventors: Peijun Cong, San Jose, CA (US);
Shenheng Guan, Palo Alto, CA (US);
Stephen Cypes, San Jose, CA (US);
Jason Wells, San Francisco, CA (US);
H. Sam Bergh, San Francisco, CA (US)

(73) Assignee: Symyx Technologies, Inc., Sunnyvale, CA (US)

( * ) Notice: Subject to any disclaimer, the term of this patent is extended or adjusted under 35 U.S.C. 154(b) by 0 days.

(21) Appl. No.: 10/900,612

(22) Filed: Jul. 28, 2004

(65) Prior Publication Data

US 2005/0056787 A1 Mar. 17, 2005

Related U.S. Application Data

(60) Provisional application No. 60/490,798, filed on Jul. 28, 2003.

(51) Int. Cl.
*G01J 3/10* (2006.01)
*G01K 11/00* (2006.01)
*G01K 13/02* (2006.01)
*G01K 25/00* (2006.01)
*G01N 31/00* (2006.01)

(52) U.S. Cl. .................. 374/131; 374/120; 374/141; 374/16; 702/23; 422/171; 356/319

(58) Field of Classification Search ............... 374/130, 374/131
See application file for complete search history.

(56) References Cited

U.S. PATENT DOCUMENTS

| | | | | |
|---|---|---|---|---|
| 2,933,600 A | * | 4/1960 | Spracklen et al. | 250/345 |
| 3,725,702 A | * | 4/1973 | Schaefer | 250/343 |
| 3,957,372 A | * | 5/1976 | Jowett et al. | 356/51 |
| 3,958,122 A | * | 5/1976 | Jowett et al. | 250/346 |
| 4,004,146 A | * | 1/1977 | Blunck | 250/345 |
| 4,048,499 A | * | 9/1977 | Kreuzer | 250/344 |
| 4,069,420 A | * | 1/1978 | Ross | 250/341.5 |
| 4,113,434 A | * | 9/1978 | Tanaka et al. | 73/863.55 |

(Continued)

FOREIGN PATENT DOCUMENTS

EP   0 651 245   5/1995

(Continued)

OTHER PUBLICATIONS

Author: Kulkova et al. Publish Date: Publish Year:1968 vol. 9 pp. 656-658 Journal: Khim. Prom. Title: An Apparatus For Testing Catalysts Of The Oxidation Of Ethylene Into Ethylene Into Ethylene Oxide.

(Continued)

*Primary Examiner*—Gail Verbitsky

(57) ABSTRACT

A library of material samples is provided in a condition suitable for imaging using infrared (IR) spectroscopy. The samples are provided to one or more detection cells, each of the cells including or containing a reflective surface. Preferably, for imaging, an energy source (e.g. a source of infrared radiation) provides energy to the detection cells to interact with the samples. Thereafter, images (e.g., spectra) related to the samples are created based upon the interaction.

49 Claims, 19 Drawing Sheets
(6 of 19 Drawing Sheet(s) Filed in Color)

U.S. PATENT DOCUMENTS

| Patent No. | | Date | Inventor(s) | Class |
|---|---|---|---|---|
| 4,256,964 A | * | 3/1981 | Ishida et al. | 250/345 |
| 4,317,041 A | * | 2/1982 | Schenck | 250/435 |
| 4,370,553 A | * | 1/1983 | Waycaster et al. | 250/343 |
| 4,373,137 A | * | 2/1983 | Fabinski et al. | 250/343 |
| 4,549,080 A | * | 10/1985 | Baskins et al. | 250/343 |
| 4,682,031 A | * | 7/1987 | Fabinski et al. | 250/345 |
| 4,822,564 A | * | 4/1989 | Howard | 422/52 |
| 4,885,469 A | * | 12/1989 | Yamagishi et al. | 250/345 |
| 5,013,920 A | * | 5/1991 | Asano et al. | 250/343 |
| 5,055,688 A | * | 10/1991 | Fabinski | 250/344 |
| 5,170,064 A | * | 12/1992 | Howe | 250/573 |
| 5,340,987 A | * | 8/1994 | Eckles et al. | 250/345 |
| 5,357,343 A | * | 10/1994 | Lowne et al. | 356/418 |
| 5,491,344 A | * | 2/1996 | Kenny et al. | 250/461.1 |
| 5,572,032 A | * | 11/1996 | Fujiwara et al. | 250/345 |
| 5,693,945 A | * | 12/1997 | Akiyama et al. | 250/345 |
| 5,876,121 A | * | 3/1999 | Burns et al. | 374/161 |
| 5,985,356 A | | 11/1999 | Schultz et al. | 427/8 |
| 6,004,617 A | | 12/1999 | Schultz | 427/8 |
| 6,121,617 A | * | 9/2000 | Hirayama et al. | 250/345 |
| 6,137,108 A | * | 10/2000 | DeThomas et al. | 250/339.07 |
| 6,141,100 A | * | 10/2000 | Burka et al. | 356/451 |
| 6,149,882 A | | 11/2000 | Guan et al. | 422/211 |
| 6,260,997 B1 | * | 7/2001 | Claybourn et al. | 374/45 |
| 6,326,090 B1 | | 12/2001 | Schultz et al. | 428/688 |
| 6,333,196 B1 | | 12/2001 | Willson, III | 436/37 |
| 6,369,387 B1 | * | 4/2002 | Eckles | 250/343 |
| 6,410,331 B1 | | 6/2002 | Schultz | 436/37 |
| 6,410,332 B1 | | 6/2002 | Desrosiers et al. | 436/37 |
| 6,426,226 B1 | * | 7/2002 | Senkan | 436/37 |
| 6,483,112 B1 | * | 11/2002 | Lewis | 250/339.02 |
| 6,514,764 B1 | | 2/2003 | Willson, III | 436/37 |
| 6,541,271 B1 | | 4/2003 | McFarland et al. | 436/171 |
| 6,563,117 B2 | | 5/2003 | Feygin | 250/332 |
| 6,576,470 B1 | * | 6/2003 | Windhab et al. | 436/64 |
| 6,623,968 B1 | * | 9/2003 | Willson, III | 436/37 |
| 6,623,970 B1 | | 9/2003 | Willson, III | 436/37 |
| 6,630,111 B1 | * | 10/2003 | Willson, III | 422/130 |
| 6,746,864 B1 | * | 6/2004 | McNeil et al. | 435/288.7 |
| 6,819,420 B2 | * | 11/2004 | Kuebler et al. | 356/337 |
| 6,849,460 B2 | * | 2/2005 | McFarland et al. | 436/171 |
| 6,853,452 B1 | * | 2/2005 | Laufer | 356/436 |
| 2002/0001080 A1 | * | 1/2002 | Miller et al. | 356/326 |
| 2002/0048536 A1 | | 4/2002 | Bergh et al. | 422/130 |
| 2002/0179834 A1 | | 12/2002 | Feygin | 250/332 |
| 2002/0197731 A1 | | 12/2002 | McFarland | 436/171 |
| 2003/0133118 A1 | | 7/2003 | Braig et al. | 356/432 |
| 2004/0188622 A1 | * | 9/2004 | Yokura et al. | 250/343 |
| 2004/0256560 A1 | * | 12/2004 | Russell | 250/338.5 |

FOREIGN PATENT DOCUMENTS

| | | |
|---|---|---|
| EP | 0883806 | 8/2003 |
| WO | WO 00/51720 | 9/2000 |
| WO | WO 01/06209 | 1/2001 |

OTHER PUBLICATIONS

Author: Snively et al. Publish Date: Publish Year:2001 vol. 67 pp. 357-368 Journal: Catalysis Today Title: Chemically Sensitive Parallel Analysis Of Combinatorial Catalyst Libraries.

Author: Snively et al. Publish Date: Publish Year:2000 vol. 2 pp. 243-245 Journal: J. Comb. Chem. Title: Chemically Sensitive High Throughput Parallel Analysis of Solid Phase Supported Library Members.

Author: Snively et al. Publish Date: Dec. 15, 1999 Publish Year:1999 vol. 24 pp. 1841-1843 Journal: Optics Letters Title: Fourier-Transform Infrared Imaging Using a Rapid-Scan Spectrometer.

Author: Snively et al. Publish Date: Publish Year:2001 vol. 40 pp. 3028-3030 Journal: Angew. Chem. Int. Ed. Title: Parallel Analysis of the Reaction Products from Combinatorial Catalyst Libraries.

Author: Lauterbach et al. Publish Date: Publish Year: Volume: Pages: Journal: Presentation Title: Rapid Scan FTIR Imaging for High Throughput Screening, no date.

Author: Castellan Publish Date: Publish Year:1983 vol. 3rd ed. pp. 625-658 Journal: Physical Chemistry Title: Molecular Spectroscopy.

Author: Publish Date: Publish Year: Volume: Pages: Journal: Presentation Title: Option 1&2: Non-Silicon Material 1R Window, no date.

Author: Billmeyer Publish Date: Publish Year: 1971 vol. 2nd ed. pp. 106-111 Journal: Textbook of Polymer Science Title: Analysis and Testing of Polymers—Polymer Chains and Their Characterization.

Author: Kubanek et al. Publish Date: Publish Year: Volume: Pages: Journal: unknown, Title: Focal Plane Array Detector Based FTIR Methods for the Parallelized Characterization of Solid Catalysts, no date.

Author: Caruthers et al. Publish Date: Publish Year:2003 vol. 216 pp. 98-109 Journal: Journal of Catalysis Title: Catalyst Design: Knowledge Extraction from High-Throughput Experimentation.

Author: Schuth Publish Date: Publish Year:2002 Volume: Pages: Journal: unknown Title: 2.3.3 Research Area "Combinatorial Catalysis and Novel Reactor Concepts".

Author: Busch et al. Publish Date: Publish Year: Volume: Pages: Journal: ABSTRACT Title: Real Time Parallel Analysis of Catalysts, no date.

Author: Kubanek Publish date: Publish Year:2004 vol. 6 pp. 420-425 Journal: J. Comb. Chem. Title: Imaging Reflection IR Spectroscopy as a Tool to Achieve Higher Integration for High-Throughput Experimentation in Catalysis Research.

Author: Leugers Publish Date: Publish Year:2003 vol. 5 pp. 238-244 Journal: J. Comb. Chem. Title: High-Throughput Analysis in Catalysis Research Using Novel Approaches to Transmission Infrared Spectroscopy.

* cited by examiner

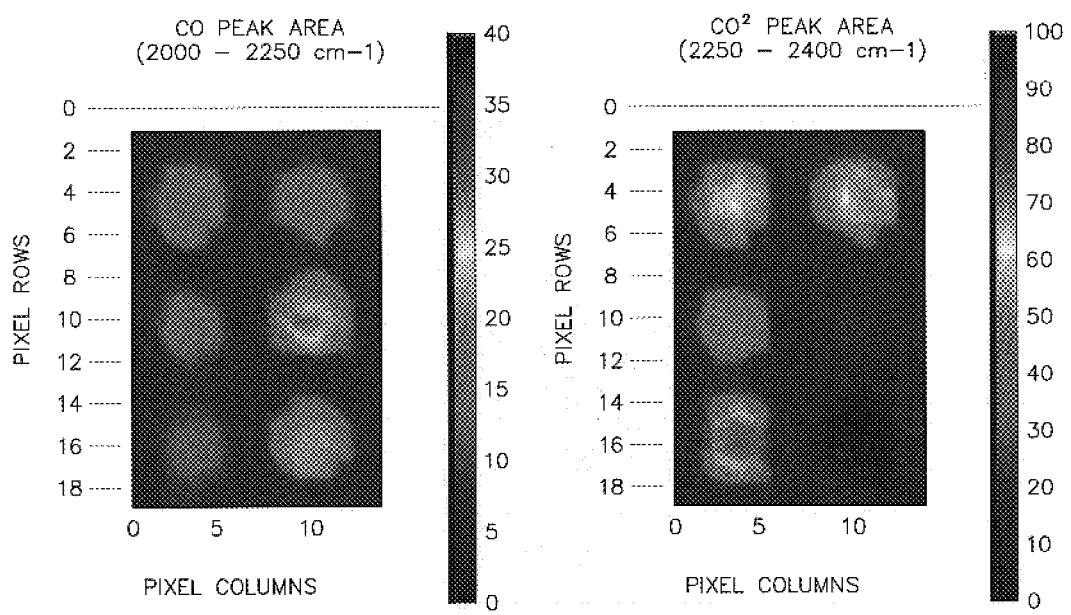

PARALLEL INFRARED SPECTROSCOPY APPARATUS AND METHOD

This application claims the benefit of and right of priority to co-owned, now abandoned U.S. provisional application Ser. No. 60/490,798 entitled Parallel Infrared Spectroscopy Apparatus and Method, filed Jul. 28, 2003 by Cong et al. under 35 U.S.C. §119(e).

TECHNICAL FIELD

The present invention generally relates to a method and apparatus for screening an array of diverse materials and/or an array of diverse chemical reactions, and, in particular, to the characterization of reaction products or unreacted reactants from parallel chemical reactions (effected for example using combinatorial libraries of diverse catalyst materials) using spectroscopic techniques, especially infrared spectroscopic techniques.

BACKGROUND OF THE INVENTION

Currently, there is substantial research activity directed toward the discovery and optimization of reactions and reactions products for a wide range of applications. Although the chemistry of many reactions has been extensively studied, few general principles have emerged that allow one to predict with certainty a composition or structure of a material that will exhibit a desired characteristic or to predict reaction pathways that will result in a desired synthesis of a desired material. As such, there exists a need in the art for a more efficient, economical and systematic techniques and apparatus for the synthesis of materials and for the screening of such materials and for screening reactions that form such materials.

Combinatorial material science refers generally to methods for synthesizing a collection of chemically diverse materials and to methods for rapidly testing or screening this collection of materials for desirable performance compositions, characteristics, properties or the like. Combinatorial materials science approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, with respect to inorganic materials such as heterogeneous catalysts, U.S. Pat. Nos. 6,004,617, 5,985, 356, 6,326,090 and 6,410,331 to Schultz et al. See also U.S. Pat. No. 6,514,764 to Willson. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

Of particular interest to the present invention are combinatorial methods and apparatuses for screening of materials, including especially screening of catalysts for catalytic activity and/or selectivity. The art includes several approaches that are effective for screening catalysts, including for example, parallel thermal imaging (see, e.g., U.S. Pat. No. 6,333,196 to Willson), parallel sorbent trapping (see, e.g., U.S. Pat. No. 6,410,332 to Schultz et al. and PCT Application No. WO 00/51720 of Bergh et al.), and analysis by parallel gas-chromatography following reaction in a parallel fixed bed reactor (see, e.g., U.S. Pat. No. 6,149,882 to Guan et al., and U.S. Published Application No. 2002-0048536 of Bergh et al.). Although such approaches are effective, it is desirable to develop other, complementary analytical techniques for evaluating materials such as catalysts, and in particular, for evaluating catalytic activity and selectivity. Spectroscopic techniques, such as infrared spectroscopy (e.g., Fourier-transform infrared spectroscopy—FTIR spectroscopy) are of particular interest in view of their universal application for detecting chemical species that are present as reaction products or unreacted reactants of a chemical reaction. Other techniques, such as non-dispersive infrared (NDIR) techniques are also of particular interest for some applications.

Several approaches are known in the art for screening combinatorial libraries of materials such as catalysts, by characterization of reaction products or unreacted reactants using infrared spectroscopy. As one example, U.S. Pat. No. 6,541,271 to McFarland et al. discloses a methodology for characterizing samples on a common substrate preferably using infrared imaging techniques, including infrared spectroscopic techniques such as FTIR spectroscopy. As another example, U.S. Pat. No. 6,623,970 (and corresponding European Patent No. EP 0883806) to Willson discloses general methods and reactor apparatus for evaluating diverse catalysts by detecting reaction products or unreacted reactants using spectroscopy, including infrared spectroscopic techniques such as FTIR spectroscopy. As a further example, International Publication Number WO 01/06209 to Lauterbach et al. is directed toward the creation of Fourier Transforms by operating a spectrometer in either a step scan or rapid scan mode. However, additional challenges remain for more effectively applying infrared spectroscopy to the analysis of materials such as reaction products or unreacted reactants resulting from parallel combinatorial reactions, such as catalyzed reactions. In particular, some of the present approaches are limited with respect to sensitivity for measuring small amounts of reaction constituents. Also, some of the approaches are limited with respect to their ability to be effectively integrated with highly parallel reaction systems, such as massively parallel microreactors.

SUMMARY OF THE INVENTION

In accordance with one preferred first embodiment of the present invention, there is provided an apparatus comprising a parallel infrared detection system for simultaneously analyzing at least two flowing fluid samples. The detection system comprises at least two detection cells, each of the at least two detection cells comprising (i) a detection cavity having one or more radiation reflective surfaces (e.g., infrared reflective surfaces) for reflecting infrared radiation, (ii) an inlet port for receiving one of the at least two samples into the detection cavity, and (iii) an outlet port for discharging the sample from the detection cavity. Preferably, the one or more reflective surfaces can be effective for reflecting at least about 50% and preferably at least about 75% of the radiation of interest (e.g., infrared radiation) under the operating conditions of interest, more preferably at least about 90%, even more preferably at least about 95% and still more preferably at least about 98%, and most preferably at least about 99% of the radiation of interest under the operating conditions of interest.

In one preferred aspect of this first embodiment, the one or more reflective surfaces can include a reflective end surface of the detection cavity. For example, the detection cavity can be an elongated detection cavity comprising a first end defined by an infrared-reflective end surface, and preferably, a second end defined by an infrared-transparent window. In this aspect of the invention, the detection cells can be particularly adapted for reflectance-mode spectroscopy.

In another preferred aspect of this first embodiment, the one or more reflective surfaces can include a reflective side surface of the detection cavity. For example, the detection cavity can be an elongated detection cavity comprising an elongated side surface effective for guiding an infrared wave of radiation along an elongated cavity (e.g., a wave guide). In this aspect of the invention, the detection cells can be particularly adapted for either reflectance-mode spectroscopy or transmission mode spectroscopy.

In a further preferred aspect of this first embodiment, the one or more reflective surfaces can include both a reflective end surface of the detection cavity and a reflective side surface of the detection cavity. For example, the detection cavity can be an elongated detection cavity that combines the infrared-reflective end surface and the wave-guiding side surface as described in the aforementioned aspects of this embodiment. In this aspect of the invention, the detection cells can be particularly adapted for reflectance-mode spectroscopy.

Further details of the detection cavity and the one or more reflective surfaces, including integration thereof with fluid distribution systems and subsystems, are described below, and can be applied with this first embodiment as well as with any of the various preferred aspects of this embodiment.

In a particularly preferred aspect, for example, the inlet port to the detection cell can be situated at the end surface, or alternatively, at the reflective side surface at a position near or proximate to the reflective end surface.

In another particularly preferred aspect, for example, in a detection cell comprising an elongated detection cavity comprising a first end and a second end defined by an infrared transparent window, the outlet port of the detection cell can be situated at the infrared transparent window, or alternatively, proximate to the infrared transparent window. For example, the outlet port can be situated at an elongated side surface at a position proximate to the infrared transparent window. Alternatively for example, the outlet port can be defined by a spaced relationship (e.g., a gap) between an open end of the elongated side surface and the infrared transparent window.

In an additional particularly preferred aspect, for example, the detection system can further comprise a pressure chamber in fluid communication with the outlet port of each of the at least two detection cavities of the two or more detection cells. Preferably, the pressure chamber can be adapted for operating conditions comprising a pressure of at least about 40 psig, preferably at least about 100 psig, and for a temperature of at least about 40° C., preferably at least about 100° C. A pressure regulator can be employed for regulating the pressure in the pressure chamber. The pressure chamber can include a sweep system comprising a sweep gas source, an inlet port in fluid communication with the sweep gas source for admitting the sweep gas into the pressure chamber, an outlet port for discharging the sweep gas out of the pressure chamber.

In a further particularly preferred aspect, for example, in a detection cell comprising an elongated detection cavity and including an elongated reflective side surface (e.g., a wave guide), at least a portion of the elongated detection cavity can be non-linear, the non-linear portion of the elongated detection cavity comprising for example a non-linear elongated reflective side surface (e.g., a flexible waveguide).

In yet an additional particularly preferred aspect, for example, in a detection system comprising two or more detection cells, with each of the two or more detection cells comprising an elongated detection cavity comprising a first end and a second end, and including an elongated reflective side surface (e.g., a wave guide), the at least two detection cells can be configured in relative relation to each other to have a first-end pitch defined by the center-to-center distance between adjacent detection cavities at the first end thereof, and a second-end pitch defined by the center-to-center distance between adjacent detection cavities at the second end thereof, with the first-end pitch of the at least two detection cells being greater than the second-end pitch of the at least two detection cells.

In any case, the detection system of this first embodiment also comprises one or more infrared radiation sources for simultaneously irradiating each of the at least two samples with infrared radiation in the detection cavity of their respective detection cells. The one or more infrared radiation sources and the one or more infrared reflective surfaces are typically configured such that infrared radiation reflects off of the one or more infrared reflective surfaces within the detection cavity of each of the detection cells.

In any case, the detection system of this first embodiment also typically includes a detector configured for simultaneously detecting reflected infrared radiation from each of the detection cells over time for analysis of the samples. The detector can include, for example, a focal plane array configured for detecting infrared radiation for each of the two or more detection cells through an infrared transparent window (e.g., the infrared transparent window of an elongated detection cavity, as described above).

In still a further particularly preferred aspect of this first embodiment, for example, in a detection cell comprising an elongated detection cavity and including an elongated reflective side surface (e.g., a wave guide), the detector can comprise a focal plane array. Preferably, the focal plane array comprises at least four pixels per detection cell of the detection system. For example, in a detection system comprising at least two detection cells, the focal plane array can comprise at least eight pixels, with the focal plane array and the detection cells being configured, for each of the at least two detection cells, for receiving infrared radiation from the detection cell into at least four pixels of the focal plane array. Additionally or alternatively, the focal plane array and the detection cells can also be preferably configured such that at least about 50% of the total number of pixels of the focal plane array receive reflected infrared radiation from a detection cell.

In a second embodiment, the invention comprises a system for simultaneously evaluating flow reactions, and preferably for simultaneously evaluating independent flow reactions having at least one parameter that varies as compared between different parallel reactions (e.g., different catalyst compositions, different catalyst support materials, different catalyst loadings, etc., and/or different reaction conditions such as temperature, pressure, space velocity, etc.) The system comprises the parallel infrared detection system (such as described above in the first embodiment, or as described below in additional embodiments) in combination with a sample source. For example, one preferred apparatus includes a sample source comprising a parallel flow reactor comprising two or more reactors, each of the two or more reactors comprising a reaction cavity for carrying out a chemical reaction, an inlet port in fluid communication with the reaction cavity for providing a feed stream comprising one or more reactants to the reaction cavity, and an outlet port in fluid communication with the reaction cavity for discharging an effluent stream comprising one or more reaction products, and optionally unreacted reactants. The preferred apparatus also includes a fluid distribution system comprising a feed distribution subsystem for simultaneously supplying the feed stream to the inlet port of each of the two or more reactors, and an effluent distribution subsystem for discharging the effluent stream from the outlet port of each of the two or more reactors. The effluent distribution subsystem is preferably configured such that at least a portion of the discharged effluent stream of one of the two or more reactors is provided as a flowing fluid sample to the inlet port of a respective one of the detection cells. In preferred aspects of this embodiment, the effluent distribution subsystem is configured such that at least a portion of the discharged effluent streams of each of two or more reactors is simultaneously provided as a flowing fluid sample to the inlet port of each of respective two or more detection cells.

According to one preferred third embodiment, the at least two detection cells of the parallel infrared detection system of the first embodiment comprise an elongated detection cavity comprising a first end defined by an infrared-reflective end surface for reflecting infrared radiation, a second end defined by an infrared-transparent window and an elongated side surface between the first end and the second end. In this embodiment, the inlet port has an opening to the detection cavity positioned at the infrared-reflective end surface. Preferably, the infrared radiation reflects off of the infrared-reflective surface of each respective detection cavity for interacting with the fluid samples. The various particularly preferred aspects described above in connection with the first embodiment can also be used in combination with this third embodiment, including for example, one or more of the particularly preferred aspects relating to (i) the outlet port of the detection cell(s), (ii) the pressure chamber, (iii) the non-linear elongated detection cavity including a non-linear elongated reflective side surface, (iv) the configuration involving the first-end pitch being greater than the second-end pitch, (v) the focal plane array detector and detection cells being configured such that there are at least four pixels of the detector per detection cell, and/or such that at least about 50% of the total number of pixels of the focal plane array receive reflected infrared radiation from a detection cell, and (vi) various combinations thereof.

According to a preferred fourth embodiment, which can be considered additionally to (i.e., in combination with) or alternatively to the third embodiment, the at least two detection cells of the parallel infrared detection system of the first embodiment comprise an elongated detection cavity comprising a first end defined by an infrared-reflective end surface for reflecting infrared radiation, a second end defined by an infrared-transparent window and an elongated side surface between the first end and the second end. In this embodiment, the elongated side surface may be effective for guiding (e.g., by reflection) an infrared wave of radiation along the elongated cavity. The various particularly preferred aspects described above in connection with the first embodiment can also be used in combination with this fourth embodiment, including for example, one or more of the particularly preferred aspects relating to (i) the inlet port of the detection cells, (ii) the outlet port of the detection cell(s), (iii) the pressure chamber, (iv) the non-linear elongated detection cavity including a non-linear elongated reflective side surface, (v) the configuration involving the first-end pitch being greater than the second-end pitch, (vi) the focal plane array detector and detection cells being configured such that there are at least four pixels of the detector per detection cell, and/or such that at least about 50% of the total number of pixels of the focal plane array receive reflected infrared radiation from a detection cell, and (vii) various combinations thereof.

In another preferred fifth embodiment, in the parallel infrared detection system of any of the aforementioned embodiments (including apparatus, systems and/or method embodiments), each of the detection cavities, the one or more infrared sources, the infrared-transparent window of each detection cavity, and the one or more detectors are configured such that the detection system has a sensitivity of measurement or detection limit below about 1000 ppm, more preferably below about 500 ppm, even more preferably below about 100 ppm and still more preferably below about 10 ppm. For these sensitivities, it is preferable that measurements are performed with a measurement error of no greater than about 500 ppm, more preferably no greater than about 100 ppm, even more preferably no greater than about 10 ppm and still more preferably no greater than 1.0 ppm above or below an actual concentration within each of the samples. As used herein, ppm (parts per million) may indicate sensitivities for concentrations derived from various measurement techniques, generally on a molar basis, but are preferably sensitivities for concentrations determined by partial pressures, particularly for gasses.

According to the present invention there is also provided a method of performing parallel infrared detection for simultaneously analyzing at least two flowing fluid samples. The method includes the provision of at least two detection cells of the type described above. Then, according to the method, at least two fluid samples respectively flow through the inlet port of each of the detection cells into the detection cavity. While the samples are in the detection cells, infrared radiation is preferably directed through an infrared transparent window into the detection cavity of each of the detection cells such that the infrared radiation reflects off of the one or more infrared reflective surfaces within the detection cavity of each of the detection cells and respectively interacts with each of the at least two samples for simultaneously irradiating the at least two samples with reflected infrared radiation. After interaction, the reflected infrared radiation from each of the detection cells is detected over time for analysis of the samples. The at least two fluid samples are preferably removed from the detection cells by respectively flowing the samples out of the detection cavity of each of the detection cells via the outlet port of each of the detection cells. The methods of the invention can be effected using any of the various aforementioned embodiments. In preferred methods, the various particularly preferred aspects described above in connection with the first embodiment can also be used to effect the methods of the invention, including for example, using one or more of the particularly preferred aspects relating to (i) the inlet port of the detection cell(s), (ii) the outlet port of the detection cell(s), (iii) the pressure chamber, (iv) the non-linear elongated detection cavity including a non-linear elongated reflective side surface, (v) the configuration involving the first-end pitch being greater than the second-end pitch, (vi) the focal plane array detector and detection cells being configured such that there are at least four pixels of the detector per detection cell, and/or such that at least about 50% of the total number of pixels of the focal plane array receive reflected infrared radiation from a detection cell, and (vii) various combinations thereof.

In yet a further set of embodiments, corresponding methods and apparatus are contemplated in a first instance, in which the infrared spectroscopy is effected in a transmission mode through an elongated detection cell having a reflective side surface (e.g., such as a reflecting elongated waveguide, rather than in a reflectance mode off of a reflective endplate), and additionally or alternatively in a second instance, in which the detection cell is a batch detection cell (for example, in which a sample such as a solid sample or a fluid sample is contained within a detection chamber, rather than flowing through a detection chamber), and in each such instance especially, for example, where the analysis and/or detector is further characterized by one or more of the particularly preferred aspects (as discussed in detail above), especially as relating to (i) the non-linear elongated detection cavity including a non-linear elongated reflective side surface, (ii) the configuration involving the first-end pitch being greater than the second-end pitch, (iii) the focal plane array detector and detection cells being configured such that there are at least four pixels of the detector per detection cell, and/or such that at least about 50% of the total number of pixels of the focal plane array receive reflected infrared radiation from a detection cell, and (iv) various combinations thereof. Hence, for example, an apparatus of the invention can comprising a parallel infrared detection system for simultaneously analyzing at least two samples, such as solid samples or fluid samples. The detection system comprises at least two detection cells, each of the at least two detection cells comprising an elongated detection cavity having an elongated radiation reflective side surface (e.g., an infrared reflective side surface), such as a capillary waveguide. Preferably, the elongated radiation reflective side surface can be effective for reflecting at least about 50% and preferably at least about 75% of the radiation of interest (e.g., infrared radiation) under the operating conditions of interest, more preferably at least about 90%, even more preferably at least about 95% and still more preferably at least about 98%, and most preferably at least about 99% of the radiation of interest under the operating conditions of interest. In one aspect of this embodiment, the detection cell is a batch detection cell. In another aspect of this embodiment, the detection cell is a flow detection cell. In a further aspect of this embodiment, each of the two or more detection cells further comprise a first radiation-transparent (e.g., an infrared-transparent window) defining a first end of the detection cell, and a second radiation-transparent (e.g., an infrared-transparent window) defining a second end of the detection cell. It is to be understood that any of these aspects of this embodiment of the invention can be used in various combination with each other, as well as with any of the previously discussed characterizing features (as generally described herein), including especially as relating to (i) the non-linear elongated detection cavity including a non-linear elongated reflective side surface, (ii) the configuration involving the first-end pitch being greater than the second-end pitch, (iii) the focal plane array detector and detection cells being configured such that there are at least four pixels of the detector per detection cell, and/or such that at least about 50% of the total number of pixels of the focal plane array receive reflected infrared radiation from a detection cell, and (iv) various combinations thereof.

It should be understood that any of the embodiments discussed above may be combined or integrated with any other of the above embodiments. For example, any of the above embodiments of detection cells may receive samples form a parallel reactor such as is described with reference to the second embodiment. Also, Fourier transform infrared analysis can be used with any of the above mentioned apparatus or method embodiments as discussed in more detail hereinafter.

It should also be understood that the above embodiments can provide one or more of a variety of advantages. As one example, certain embodiments of the methods and apparatus above can improve the sensitivity and/or accuracy of measurements such as concentration measurements, partial pressure measurements or the like. As another example certain embodiments of the methods and apparatus above provide for simplified integration or fluid communication of flow reactors with the detection cells. As still another example, certain embodiments of the methods and apparatus above provide for more detection cells in a smaller amount of space.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 8A through 8E show the experimental spatial configuration (FIG. 8A) and experimental data (FIGS. 8B through 8E) resulting from a set of experiments investigating six different catalysts (Catalyst A through Catalyst F, FIG. 8A) and involving simultaneous analysis of six effluent streams from a six-channel parallel flow reactor at four different temperatures—at 40° C. (FIG. 8B), at 100° C. (FIG. 8C), at 140° C. (FIG. 8D), and at 180° C. (FIG. 8E)), as described in Example 2, using a detection system configured substantially as described in connection with FIG. 1 and including a detection cell unit substantially as described in connection with FIGS. 2C, 2D and 7A through 7C.

DETAILED DESCRIPTION OF THE PREFERRED EMBODIMENT

Figure 1:
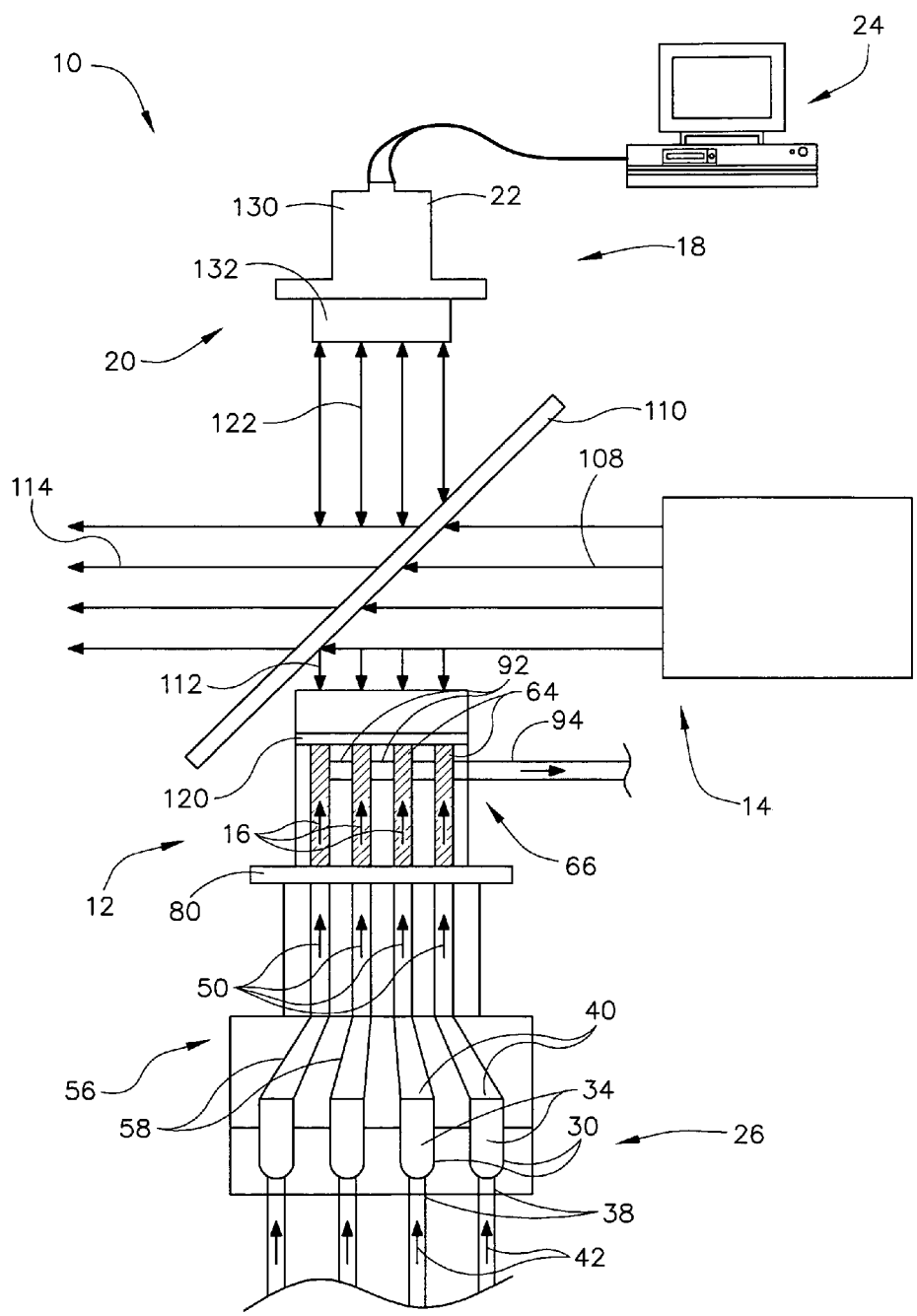
FIG. 1 is a schematic diagram of an exemplary detection system for screening material samples according to a preferred aspect of the present invention.

As used herein, the term "radiation" is intended to generally refer to energy with a wavelength between $1\times10^6$ meters and $1\times10^{-2}$ nanometers. Examples of such radiation include electron beam radiation, gamma radiation, x-ray radiation, ultraviolet radiation, visible light, infrared radiation, microwave radiation, and radio waves. Irradiation refers to the application of radiation to a material or object, and in the context of this application, to a sample or component thereof being analyzed with the detection system.

Apparatus and Methodology

Generally, the present invention is directed to an apparatus and a methodology for screening material samples. Typically, the apparatus includes an energy source for supplying energy to the material samples, and a detection system for detecting the energy after is has been exposed or otherwise interacted with the samples. The detection system also typically includes one or more detection cells configured for operating in a reflectance mode (i.e., generally configured for reflecting energy within the detection cell). As such, each of the detection cells preferably includes at least one reflective surface capable of reflecting the energy from the energy source. Advantageously, it has been found that the reflected or refracted energy provided by the detection cells can assist a detector in taking measurements with greater sensitivity and/or accuracy when performing measurements on the samples thereby allowing more probing analysis of samples. Such sensitivity can be particularly helpful for taking concentration measurements of one or more components (e.g., reaction products) in the samples.

The detections cells of the present invention may be formed in a variety of configurations and may be formed of a variety of material. Each of the detection cells will typically provide an elongated (e.g., tubular) structure with a detection cavity. Preferably, each detection cell is elongated and extends between a first end and a second end, although not required. Generally, samples may be provided as substantially stationary within the detection cavity (e.g., in a batch detection cell) or the samples may be flowing through the detection cavity (e.g., in a flow detection cell). Preferably, each of the detection cells (whether flow detection cells or batch detection cells) are substantially isolated from each other, so that cross-talk between adjacent cells is minimized (e.g., to limits acceptable for the particular evaluation of interest), and so that each of such detection cells, taken together with other corresponding components of the detection system (e.g., interferometer, etc. as described herein) are part of a detection channel dedicated to a particular sample contained (at least for some detection period of time, e.g., in batch or flow mode) within that detection cell.

In a preferred embodiment, each detection cell includes an inlet and an outlet such that samples can flow into the detection cavity through the inlet, through the elongated (e.g., tubular) structure and cavity and out of the cavity through the outlet. The inlet and outlet may be located as desired for the detection cell, however, it is preferable for the inlet and outlet to be located at, or proximate to the respective ends of the detection cells such that the samples flow substantially through a length of the cells.

Generally, each of the detection cells typically includes one or more reflective surfaces, and particularly reflective surfaces capable of reflecting energy (e.g., infrared radiation) of the energy source. Preferably, the one or more reflective surfaces are located within the detection cells and/or assist in defining the cavities of the detection cells. Particular features of the reflective surfaces are described below, and as described are to be considered generally applicable to each of the embodiments and aspects of the invention.

The two or more detection cells may be structurally integrated (i.e., interconnected) with each other using a variety of structures, to form a detection cell unit. For example, the detection cells may be defined as a plurality of openings in a single mass of material (e.g., such as a monolithic block) such that the single mass defines plural elongated (e.g., tubular) structures. Alternatively, the detection cells may be formed of a plurality of separate elongated (e.g., tubular) structures that are attached to each other by one or more other structure (e.g., a frame, a support or the like), for example, at the ends or bodies of the elongated (e.g., tubular) structures.

Fluid samples, when used, are typically provided to the detection cells using a fluid distribution system. The fluid distribution system typically includes one or more structures providing channels between a sample source and the detection cells. The fluid distribution system can include a feed distribution subsystem for supplying the samples (e.g., continuously or intermittently) to the inlets of the detection cells and/or a sample receiving subsystem for receiving the samples from the sample source. Moreover, the fluid distribution system and its subsystems may be formed as multiple components or as one or more integrated structures. The fluid distribution system may provide substantially all of a sample source to the detection cell, or may provide a portion of a sample source to the detection cell. For example, where the sample is a fluid, and where the sample sources are a set of flowing fluid streams, it may be desirable to employ flow splitters or other sampling means in connection with the fluid distribution system for supplying each of the sample streams to a corresponding detection channel of the detection system. Also, it may be desirable to process a sample, such as a set of sample streams, prior to introduction to the detection system. Such processing can include separation (e.g., using parallel chromatography, for example) and/or dilution (e.g., using a dilution manifold, for example).

The energy source of the system can also be provided in a variety of configurations. Preferably, the energy source provides energy in the form of radiation and more preferably in the form of infrared radiation, although not required.

Generally, the energy source provides its energy to the detection cells for interaction with the samples in the cells. Preferably, the energy source provides the energy to the detection cavities of the detection cells such that the energy reflects off the one or more reflective surfaces to form reflected radiation that interacts with the samples in the detection cells.

The detection system of the apparatus can be configured as desired as long as it has the ability to detect the energy of the energy source and particularly the energy that has been reflected from the one or more reflective surfaces of the detection cells. Preferably, the detection system is an imaging system that can create images base upon radiation (e.g., infrared radiation) detected by the system. Thus, the reflected energy from the detection cells can be detected and imaged continuously or intermittently over time, including at least one time period, which is particularly useful for detection of flowing fluid samples. As a preferred example, the detection system may be comprised of a Fourier Transform Infrared (FTIR) detection system including a camera for capturing radiation images, a focal plane array for focusing the images on the lens of the camera, and a processor capable of performing fourier transformation. As another example, the detection system can be configured for other techniques, such as non-dispersive infrared (NDIR) techniques, and can include at least a camera for capturing radiation images, a focal plane array and a processor.

Preferably, the detection system has a sensitivity of measurement or detection limit below about 1000 ppm, more preferably below about 500 ppm, even more preferably below about 100 ppm and still more preferably below about 10 ppm. For these sensitivities, it is preferable that measurements are performed with a measurement error of no greater than about 500 ppm, more preferably no greater than about 100 ppm, even more preferably no greater than about 10 ppm and still more preferably no greater than 1.0 ppm above or below an actual concentration within each of the samples. Although the aforementioned sensitivities are preferred generally, such sensitivities can be measured, for purposes of characterizing the detection system, with respect to a particular analyte, such as carbon monoxide (CO).

Figure 2A:
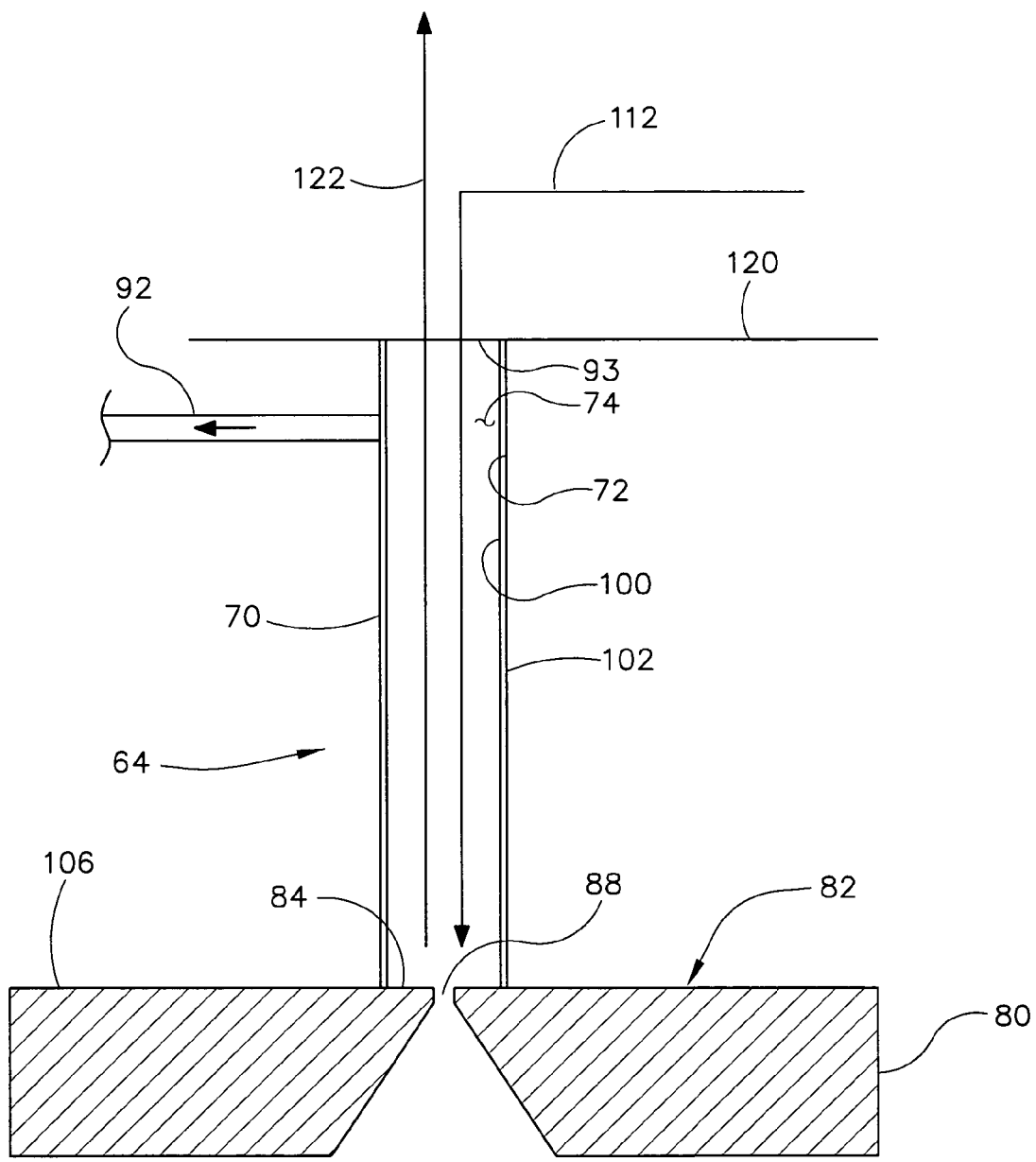
FIGS. 2A through 2D are schematic diagrams of various alternative detection cell embodiments, illustrating a single detection cell (FIGS. 2A, 2B and 2C) or multiple detection cells (FIG. 2D), which can be configured for use in connection with the detection system of FIG. 1.

FIGS. 1 and 2A schematically illustrates a system 10 including an IR imaging apparatus 12 for performing IR imaging of material samples according to the present invention. The apparatus 10 includes an energy source 14 for providing energy to a library of material samples 16 and a detection system 20 having a detector 22 for detecting the energy after it interacts with (e.g., irradiates) the samples 16. As shown, the detection system 20 is in communication with a processor 24 (e.g., a computer), which is configured for assisting in analyzing the energy detected by the detector 22.

The samples 16 are provided by a sample source, and it is generally contemplated that the samples 16 may be provided in a variety of configurations or conditions. For example, the samples 16 may be provided as fluids, gasses, liquids, solids or combinations thereof and may be provided in a stationary condition, a dynamic condition or a combination thereof. According to a preferred embodiment, the samples 16 are provided as moving (e.g., flowing fluids).

The number of samples 16 provided will typically depend upon the capabilities of detection system 18. Generally, it is contemplated that a sample source according to the present invention can serially or simultaneously provide nearly any number of desired samples for carrying out analysis of samples for analytical purposes, including for quality assurance or research purposes, including for example combinatorial (i.e., high-throughput) research. As examples, it is contemplated that the sample source is capable of providing at least 2 samples, more preferably at least 4 samples, even more preferably at least 16 samples and still more preferably at least 48 samples, and respectively, the detection system is capable of simultaneously analyzing such samples in a corresponding number of separate detection cells.

In the embodiment illustrated, the sample source(s) is(are) provided as a reactor(s) 26 such that the samples 16 are provided at least partially as reaction products. While it is contemplated that various types of reactors (e.g., batch reactors) may be employed in the system 10, a preferred reactor is a flow-through type reactor of the type shown or of another type. In general, particularly preferred parallel flow reactors include parallel fixed-bed reactors, parallel trickle-bed reactors, parallel fluidized-bed reactors, configured either as single-stage or multiple-stage reactors. Exemplary, flow-through reactors, which may be suitable for use in the present invention are disclosed in U.S. Pat. No. 6,149,882 to Guan et al., PCT Application No. WO 00/51720 of Bergh et al., and U.S. Published Application No. 2002-0048536 of Bergh et al.), each of which is hereby incorporated by reference.

The reactor 26 illustrated is a typical flow-through reactor in that it includes a plurality of reaction chambers 30 that define a plurality of reaction cavities 34 configured for receiving reactants and emitting reaction products. The reactor 26 may include as few as one reaction chamber, but preferably includes multiple reaction chambers 30 and the number of reaction chambers may or may not be in correspondence to the number of desired samples. Thus, according to a preferred embodiment, 2 or more reaction chambers, more preferably 4 or more reaction chambers and even more preferably 16 or more reaction chambers for providing a corresponding number of samples.

The reaction chambers 30 illustrated each include an inlet 38 and an outlet 40 in fluid communication with the reaction cavity 34. Typically, one or more reactants 42 flow as fluid feed streams through the inlets 38 into the reaction cavities 34. While in the reaction cavities 34, the reactants 42 at least partially react to form reaction products, which are discharged from the reaction chambers 30 as effluent streams 50 via the outlets 40. Preferably, any amount of reaction that occurs between the reactants 42 occurs within the chambers 30, however, it is contemplated that reactants may at least partially react before entering, or after leaving the reaction chambers 30. It is also contemplated that a subset of the reactants may not react thereby forming an unreacted subset of samples.

After exiting the reaction chambers 30, the plurality of samples 16 are respectively provided to the detection system 20 via a fluid distribution system 56. The fluid distribution system 56 will typically include a plurality of tubular structures 58 having openings for respectively providing fluid communication between the plurality of reaction chambers 30 and the detection system 20. It is contemplated, however, that the skilled artisan will be able to conceive of a variety of fluid distribution systems within the scope of the present invention. It is also contemplated that the samples may be provided directly to the detection system from the reaction chambers without a fluid distribution system. Moreover, it is contemplated that the reaction chambers may be integrated with the detection system.

Although the preferred exemplary embodiment has been shown as including a flow through reactor as a sample source for the detection system 20, it is contemplated that, as discussed, various alternative sample sources may be employed as well. As an example, a batch reactor may be used to provide samples. As another example, it is contemplated that fluids may be provided from non-reactive systems such as a condensation or vaporization system or from a combination of a reactive system employed in conjunction with a condensation or vaporization system. In other alternative, the sample source may be an air or other gas sample source and the detection system could be employed for purposes such as environmental sample, gas quality control or the like. The sample could also be provided from one or more adsorption/desorption vessels. The sample could also be a sample from an industrial process, to be analyzed for process monitoring and/or control and/or for quality assurance.

Referring again to FIGS. 1 and 2A, the detection system 10 typically includes one or more detection cells 64 for receiving the samples 16. Preferably, there are at least as many detection cells 64 as there are samples 16 or sample sources (e.g., reactions chambers 30) such that each of the samples 16 can respectively be received its own separate detection cell 64, although such is not required. In some embodiments, for example, there may be more detection cells than samples 16 or sample sources (e.g., reaction chambers 30), such that the detection system can comprise one or more extra detection cell(s)—not aligned with a to-be-analyzed sample—but used instead, for example, as one or more spare detection cell(s) and/or as one or more reference detection cell(s). It is also preferably for the detection cells 64 to be positioned and supported as a detection cell unit 66, which may be configured as needed or desired. Preferably, the detection cell unit 66 comprises two or more structurally integrated detection cells 64. For example, a frame or other structure may secure the cells 64 together, for example, in a particular alignment with each other and/or with other aspects of the detection system.

In FIG. 2A, there is provided an enlarged schematic view of one of the detection cells 64 for describing the detail of the particular cells 64 illustrated. Of course, it should be understood that the system 10 may include as many or as few detection cells 64 as needed. As shown, each detection cell 64 includes an elongated (e.g., tubular) structure 70 having an inner surface 72 at least partially defining a detection cavity 74. In the embodiment illustrated, the tubular structure 70 is substantially cylindrical for forming the cavity 74 in a cylindrical configuration. However, various other shapes and configurations may be employed for the structure 70 and the cavity 74.

Referring to both FIGS. 1 and 2A (as well as FIG. 2C) each of the cells 64 are further defined by a base member 80, which supports each of the cells 64. As shown, the base member 80 is located at one end (e.g., a first end) of the detection cell 64 and provides a surface 82, a portion 84 of which (e.g. an end surface or portion) partially defines the cavity 74 of each of the cells 64. The base member 80 also defines an inlet 88 for each detection cell 64 for receiving the samples 16 from the sample source (e.g., the reactor 26). As shown, the inlet 88 is located proximate to, and particularly, at the end portion 84 of the cell 64. In embodiments where the inlet is located at a reflective end surface of a detection cell, such as the illustrated embodiments shown in these figures, the size of the inlet opening can be optimized with consideration given to maximizing reflectance off of the reflective end surface (warranting a smaller inlet opening) and having an acceptable pressure drop across the inlet opening (warranting perhaps a larger inlet opening). As shown in FIG. 1 and in FIGS. 2A through 2C, each of the detection cells 64 also includes an outlet 92 as well that is preferably located proximate to an end portion, particularly a second end portion 93 of the cell 64 that is opposite the other end portion 84 of the cell 64. Moreover, it is contemplated that the outlet 92 can be in fluid communication with a flow system 94 (FIG. 1, e.g., a manifold) capable of receiving and flowing the samples 16 away from the detection cells 64. As used herein, the phrase "proximate to an end surface or portion" means closer to one end surface or portion of the detection cell than to the other end surface or portion and more preferably means twice as close to one end surface or portion of the detection cell than to the other end surface or portion, and in either case, includes positions generally adjacent to or at that end surface or portion. The second end portion 93 of the detection cell can comprise a radiation-transparent window 120, that is substantially transparent to the energy being used in the detection system (e.g., allows for transmission of a substantial portion of the applied energy through the window). For example, the second end portion 93 can be an infrared transparent window 120 for a detection system using infrared radiation, such as an FTIR detection system. In one embodiment, the infrared transparent window can be a zinc selenide window, preferably having anti-reflective coating. The thickness of the radiation transparent window is not critical, and can be determined based on considerations of balancing various properties of the window for the operating conditions of interest (e.g., radiation wavelength, temperature, pressure, etc.), such as optical properties (e.g., transmission of incident and/or reflected radiation through the window) and mechanical properties (e.g., withstanding pressurization forces, for embodiments that include a pressure chamber). Generally, but without limitation, the radiation transparent window such as a zinc selenide window can have a thickness ranging from about 0.1 mm to about 5 cm, preferably from about 0.5 mm to about 3 cm, and in some cases from about 1 mm to about such as about 20 mm. The optical properties of the radiation transparent window are preferably optimized for maximum possible transmission efficiency for operation with the radiation of interest, including transmission efficiencies of at least about 75%, preferably at least about 85%, and more preferably at least about 90% transmission. Anti reflective coatings can be disposed on one or both surfaces of the radiation transparent window, as known in the art, and can improve transmission efficiencies (relative to uncoated windows); some types of coatings, however, such as polymeric coatings, may provide a constraint on operations at higher temperatures.

Figure 2B:
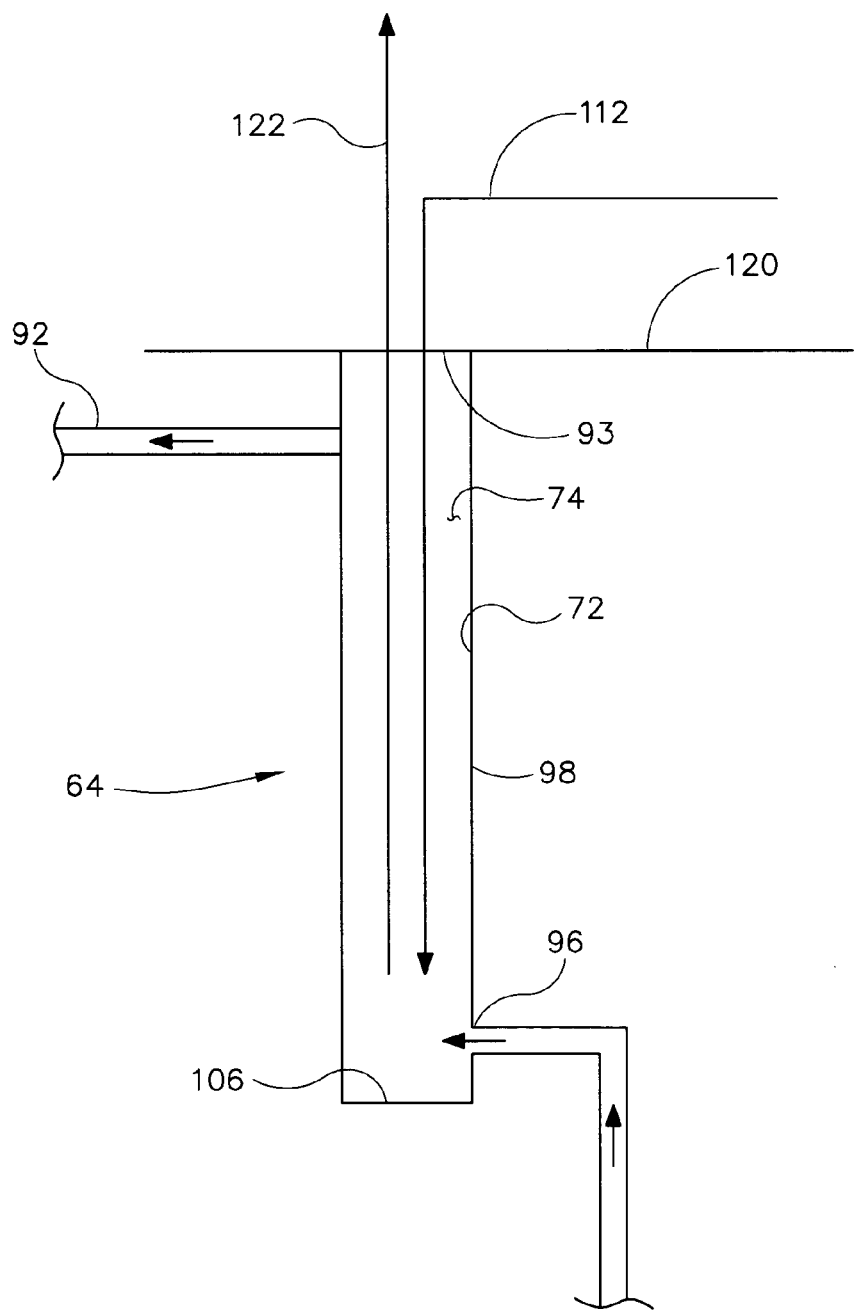

In alternative embodiments, the inlet or outlet may be located in alternative locations. For example, as shown in FIG. 2B an inlet 96 may provide fluid communication through a side wall 98 of the detection cell 64. As another example, shown schematically in FIGS. 2C and 2D, the outlet 92 can be proximate to the second end portion 93 of the detection cavity 74. In particular, as shown, the detection cell 64 comprises an elongated detection cavity 74 including a first end 84 (e.g., defined by a portion of the surface 82 of base 80), and a second end 93 (e.g., defined by a radiation transparent window 120 such as an infrared transparent window). An elongated side surface 72 is between the first end 84 and the second end 93 of the detection cavity 74. The elongated detection cavity 74 comprising an elongated side surface 72 (e.g., with reflective surface 100) can be realized using a capillary tube 102 (e.g., a capillary waveguide). The outlet port 92 of the detection cell 64 is proximate to the infrared transparent window 120 (FIG. 2D), and in particular for the illustrated embodiment, is defined by the spaced relationship (e.g., a gap) between an open end 73 of the elongated side surface 72 and the second end 93 of the detection cavity 74. The spacing between the open end 73 and the second end 93 of the detection cell 64 is not narrowly critical. In embodiments where the second end 93 is defined by a portion of the radiation transparent window 120, the spacing (gap width) can range from about 0.1 mm to about 10 cm, preferably from about 0.5 mm to about 5 cm, with more narrow ranges also being suitable, including for example from about 0.7 mm to about 3 cm or from about 1 mm to about 2 cm. Generally, gap width can be less constrained (e.g., can vary over a wider range of values, and e.g., can vary as compared between different detection cells) in detection systems that have a common effluent chamber and a sweep system, as described below. As yet another example (not shown in the figures), it is also possible to provide for flow through an elongated detection cell having an elongated detection cavity in the opposite direction, with the inlet port being located proximate to the second end of the detection cell (e.g., defined by a radiation-transparent window), and the outlet port being located proximate to or at the first end of the detection cell (e.g., defined by a reflective end surface).

Figure 2C:
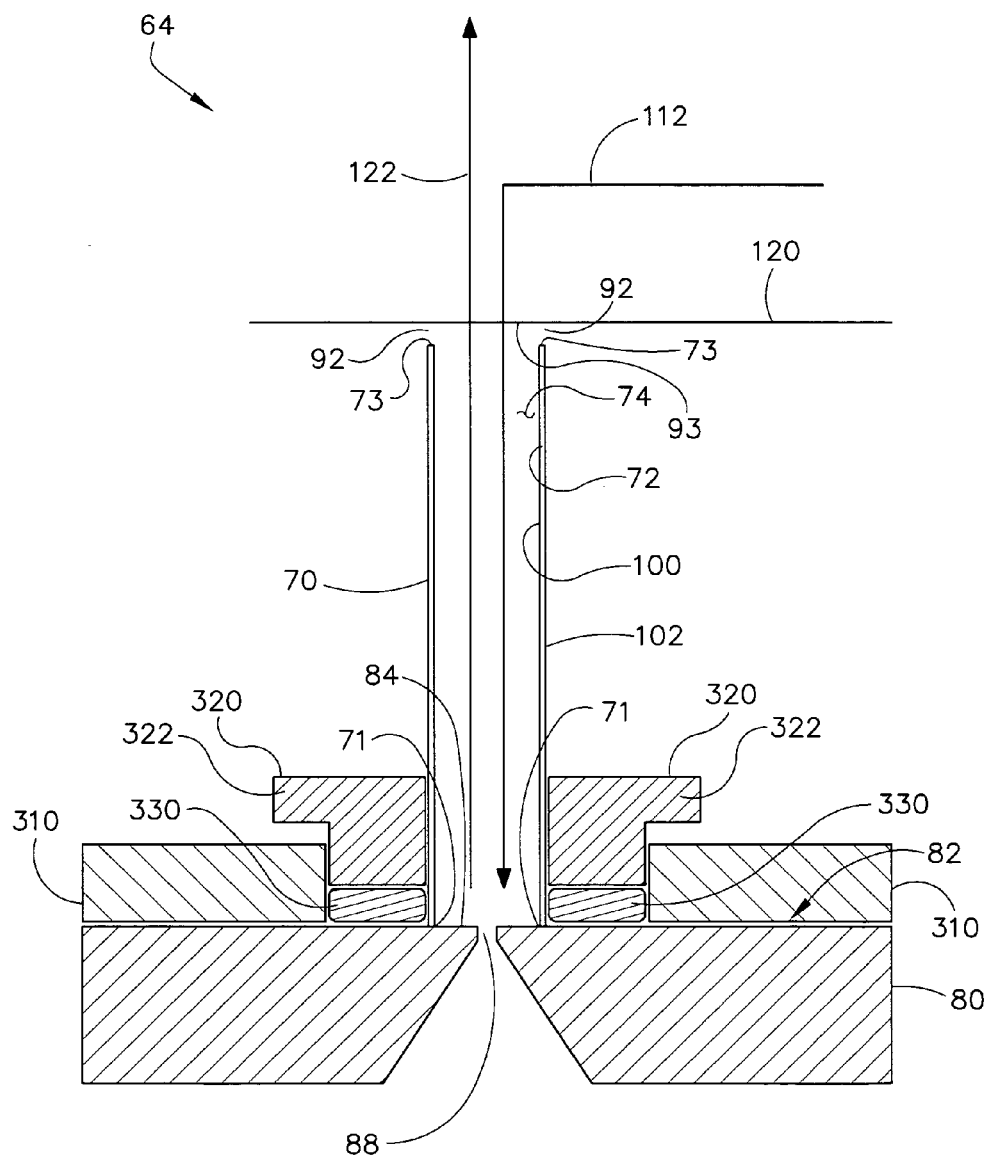
Figure 2D:
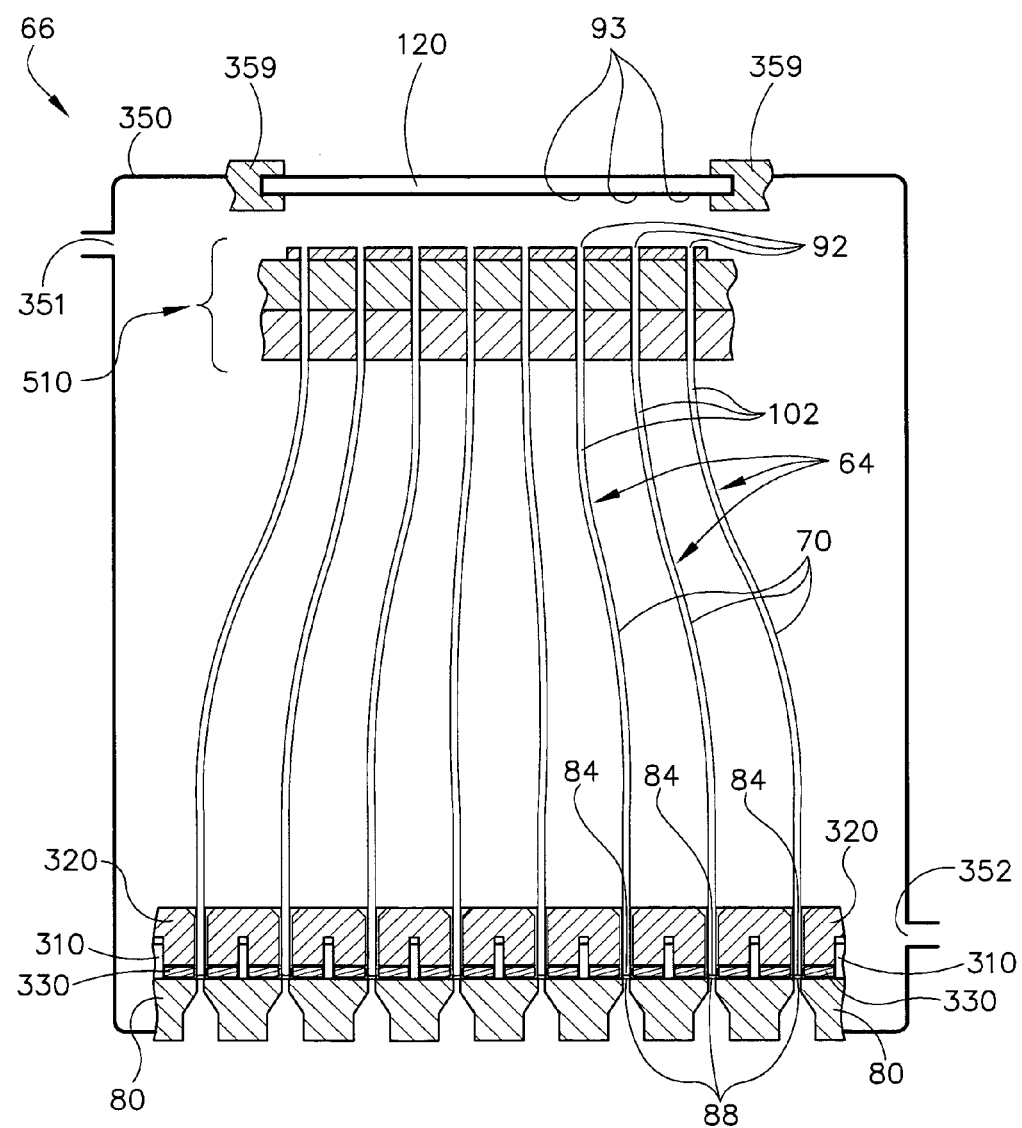

Generally (not limited to any specific embodiment), the detection cells are preferably fluidically separated/isolated from adjoining detection cells so that cross-talk between adjacently evaluated samples is minimized, and preferably substantially eliminated—to allow for effective independent analysis of separate adjacent samples. With reference to FIGS. 2C and 2D, for example, such fluidic isolation can be realized, for example, by fluidically sealing at least the first end 71 of the elongated side surface 72 of capillary 102, with the seal being effective at the operating conditions (e.g., temperature, pressure) of interest. The seal can be any suitable material, preferably a deformable material, and can be in any suitable shape, such as a gasket having apertures or a ring seal, such as an o-ring seal, as otherwise described generally herein or in connection with other specific embodiments herein. As shown in FIGS. 2C and 2D, for example, the first end 71 can be sealed using a first seal plate 310 disposed adjacent to base 80, a second seal plate 320 disposed adjacent to the first seal plate 310, and one or more seals, such as a base seal 330. As depicted in FIG. 2C, base seal 330 provides sealing contact between each of surface 82 of base 80, outside surface of capillary 102, inside surface of first seal plate 310, and bottom surface of second seal plate 320. These various sealing contacts can be enhanced by compressive forces applied between each of the base 80, the first seal plate 310 and the second seal plate 320, for example using fasteners (e.g., bolts or screws), clamps, hydraulic pressure or other compressive force means (not shown) generally known in the art.

Although not shown in FIGS. 2C and 2D, the second end 93 of the elongated side surface 72 of capillary 102 can be sealed in a manner similar to the aforedescribed sealing arrangement used in connection with the first end 71, with the seal being effective at the operating conditions (e.g., temperature, pressure) of interest. Alternatively, however, fluidic isolation of adjoining detection cells 64 can be achieved without sealing the second end 93 of each detection cell 64. For example, with further reference to FIGS. 2C and 2D, the respective outlets 92 of each detection cell 64 can be in fluid communication with a common effluent chamber (such as a pressure chamber 350). In such a configuration for the respective outlets 92, fluidic isolation between adjacent detection cells 64 can be achieved for example by use of a sweep system to flush sample effluent away from each respective outlet 92 at a volumetric flow rate sufficient to minimize and preferably avoid a detectable amount of the sample effluent from back-diffusing into the outlet 92 from which it came, and/or from diffusing into adjacent outlets 92. The sweep system of the common effluent chamber (e.g., common pressure chamber 350, as shown) can generally include a sweep gas source (not shown), an inlet port 351 in fluid communication with the sweep gas source for admitting the sweep gas into the common effluent chamber (e.g., pressure chamber 350), and an outlet port 352 for discharging the sweep gas out of the common effluent chamber (e.g., pressure chamber 350). In operation, the sweep gas can be an inert gas (i.e., non-reactive for the analyte of interest), and is preferably selected to be non-absorbing of the radiation of interest or at least minimally-absorbing of the radiation of interest (e.g., absorbing less than about 20%, preferably less than about 10%, most preferably less than about 5%) of a beam of incident radiation of interest). Also, the volumetric flow-rate of the sweep gas through the effluent chamber (e.g., pressure chamber 350) can be controlled to minimize and preferably avoid a detectable amount of the sample effluent from back-diffusing into the outlet 92 from which it came, and/or from diffusing into to adjacent outlets 92. As such, the sweep gas system can further comprise one or more flow controllers for controlling the flow rate of the sweep gas, and/or as further described generally below, one or more pressure regulators for controlling the pressure of the sweep gas within the common effluent chamber (e.g., pressure chamber 350).

Generally, the detection system of the invention can further comprise a pressure chamber in fluid communication with the outlet port of each of the at least two detection cells. Referring again to FIG. 2D, for example, pressure chamber 350 can be in fluid communication with each of the respective outlet ports 92 of detection cells 64. The pressure chamber (e.g., pressure chamber 350 as shown) can generally be adapted for operating conditions comprising a pressure of at least about 40 psig, preferably at least about 100 psig, and optionally for higher temperature operation, including for example for a temperature of at least about 40° C., preferably at least about 100° C. More particularly, the pressure can be at least about 200 psig, at least about 300 psig, at least about 500 psig, at least about 1000 psig or at least about 1500 psig. The temperature can more particularly be at least about 150° C., at least about 200° C., at least about 300° C., at least about 350° C. or at least about 400° C. A pressure regulator (not shown) can be employed in fluid communication with pressure chamber 350 for regulating the pressure therein. For embodiments in which fluid samples are provided to the detection system by fluid communication with the detection cells (e.g., as shown in FIGS. 1 and 2D, considered together), such a pressure regulator can also regulate the pressure in upstream components (e.g., reaction vessels) that are in fluid communication with the respective detection cells. A heater, such as a band heater disposed generally adjacent to pressure chamber 350 and in thermal communication (e.g., in conductive contact) therewith, can be employed in a temperature control system for controlling the temperature of the detection cells 64. Having a detection system that comprises a pressure chamber suitable for high-temperature and high-pressure operating conditions provides greater universality of the detection system, allowing evaluation of condensable fluids in the gaseous state (e.g., maintained in the gaseous state by heating), and/or allowing for evaluation under common back-pressure control.

Generally, the pressure, temperature, flow rates of sample(s), flow rates of sweep gas, and other operating conditions of the detection system can be controlled using control systems known in the art, and typically including a control system comprising a microprocessor in communication with various detectors (e.g., temperature detectors, flow detectors, pressure detectors, etc.) and/or with various control elements (heaters, flow regulators, pressure regulators, etc.).

Generally, a detection cell comprising an elongated detection cavity and including an elongated reflective side surface (e.g., a wave guide, such as a capillary wave guide) can include one or more non-linear portions of the elongated detection cavity. The non-linear portion of the elongated detection cavity can comprise for example a non-linear elongated reflective side surface (e.g., a flexible waveguide). Substantial configuration flexibility can be achieved using such non-linear detection cavities. As shown in FIGS. 2C and 2D, for example, one particularly advantageous configuration that can be realized using non-linear detection cavities (e.g., using flexible waveguides such as capillary waveguides 102), involves a detection system comprising two or more detection cells 64, with each of the two or more detection cells comprising an elongated detection cavity 74 comprising a first end 84 and a second end 93, and including an elongated reflective side surface 72. In such a detection system, the at least two detection cells 64 can be configured in relative relation to each other to have a first-end pitch defined by the center-to-center distance between adjacent detection cavities 74 at the first end 84 thereof, and a second-end pitch defined by the center-to-center distance between adjacent detection cavities 74 at the second end 93 thereof, with the first-end pitch of the at least two detection cells being greater than the second-end pitch of the at least two detection cells. As shown in FIG. 2D, the first-end pitch can be realized by appropriate spacing of first ends 84 of the respective detection cavities 74 on the base 80, with corresponding spacing to accommodate the capillary waveguides 102 disposed through the first seal plate 310 and the second seal plate 320. The second-end pitch can be similarly realized, for example by appropriate spacing of the second ends 73 of reflective side surface 72 of capillary waveguides 102 (and corresponding spacing of second ends 93 of detection cavities 74) in upper support block 510.

Significantly, having a larger first-end pitch than second-end pitch allows for a configuration that accommodates fluidic interface between two or more detection cells and the one or more sample sources at the first-end of the detection cells, and also accommodates geometric constraints and/or detection sensitivity advantages at the second end of the detection cells. For example, when using a detector comprising a focal plane array, such configuration can allow for a more efficient use of the available pixels of the focal plane array (i.e., a higher percentage of the total available pixels of the focal plane array are being at least partially used for detection) at the second end of the detection cells, for example, by allowing for close-packing of detection cells. Also, such improved pixel efficiency can be achieved independently of or concurrently with facilitating a high pixel density per detection cell at the second end of the detection cells. Each of these advantages are discussed more fully hereinafter.

Generally, when using a detector comprising a focal plane array, the focal plane array can comprise one or more pixels per detection cell of the detection system, and in preferred approaches where higher sensitivities are desired, comprises at least two pixels and preferably at least four pixels per detection cell of the detection system (i.e., the focal plane array and a particular corresponding detection cell are configured so that at least four pixels of the focal plane array receive radiation from the corresponding detection cell). More preferably, when using a detector comprising a focal plane array, the focal plane array comprises at least about eight, or at least about sixteen, or at least about twenty-five, or at least about thirty-five, or at least about fifty, or at least about seventy-five or at least about one-hundred pixels per detection cell. However, since focal plane arrays are commercially available with much higher numbers of elements (pixels)—such as focal plane arrays comprising 64×64 elements, 256×256 elements, 512×512 elements or 1024×1024 elements, and since such focal plane arrays can also have much smaller element (pixel) areas, much higher detection-cell pixel densities can be achieved in accordance with the present invention, including for example at least about 400 pixels, at least about 700 pixels, at least about 1000 pixels, at least about 2000 pixels, at least about 4000 pixels, at least about 7000 pixels or at least about 10,000 pixels per detection cell. The higher pixel density per detection cell can significantly improve the sensitivity of the detection system, since the signal:noise ratio is enhanced using higher pixel density configurations. Without being bound by theory, the sensitivity of the detection system can generally be improved, relative to a detection cell comprising a single pixel per detection cell, by a factor that is the square root of the pixel density per detection cell. For example, if the detection limit for detection of CO using a detection system having a single pixel per detection cell is about 0.1% CO (about 1000 ppm), (molar basis, as measured using partial pressure), then the detection limit can be enhanced by a factor of $(N)^{1/2}$ by using a detection system having N pixels per detection cell. Hence, for example, the detection limit for detection of CO using a detection system having sixteen pixels per detection cell (instead of one pixel per detection cell) can be enhanced by a factor of about 4, e.g., to about 0.025% CO (about 250 ppm). Similarly, for example, the detection limit for detection of CO using a detection system having one-hundred pixels per detection cell (instead of one pixel per detection cell) can be enhanced by a factor of about 10, e.g., to about 0.01% CO (about 100 ppm). Further, as noted above, it may generally be further advantageous and preferable, in embodiments using a detector comprising a focal plane array, that the focal plane array and the two or more detection cells are configured to more efficiently use the total number of pixels available in the focal plane array. Generally, for example, in embodiments using a detector comprising a focal plane array, the focal plane array and the two or more detection cells can be configured so that at least about 20% and preferably at least about 25% of the total number of pixels of the focal plane array (can and in operation will) receive radiation (e.g., reflected radiation) from a detection cell. In some instances, it will be preferable for the focal plane array and the two or more detection cells to be configured so that at least about 40%, preferably at least about 50% and more preferably at least about 60% of the total number of pixels of the focal plane array (can and in operation will) receive radiation (e.g., reflected radiation) from a detection cell. In some other instances, when using a detector comprising a focal plane array, the focal plane array and the two or more detection cells can be configured so that at least about 70%, at least about 75%, at least about 80%, at least about 85%, at least about 90% or at least about 95% of the total number of pixels of the focal plane array receive radiation (e.g., reflected radiation) from a detection cell. Such higher pixel efficient configurations can employ detection cells having geometries other than circular cross-sectional geometries (to allow for closer packing of detection cells). For example, detection cells have polygonal cross sections (such as square or rectangular or pentagonal or hexagonal or septagonal or octagonal cross sections) can be employed. Some such detection cells can be micromachined detection cells. Advantageously, higher pixel efficient configurations provides for improved detection sensitivity. Also, such higher pixel efficient configurations make it possible and cost-effective to realize high pixel densities per detection cell (as described above) even for massively-parallel detection systems, including detection systems having 50 or more detection channels, or preferably having 75 or more detection channels, or even higher numbers of channels, including for example 100 or more detection channels, 150 or more detection channels, 200 or more detection channels, 400 or more detection channels, 700 or more detection channels, 1000 or more detection channels, 4000 or more detection channels, 7000 or more detection channels or 10,000 or more detection channels.

Fluidic interface between the two or more detection cells and the one or more a sample sources (e.g., reactor effluent streams) can be provided by any convenient means. Referring to FIG. 2D, for example, fluidic interface between each of the detection cells 64 and the one or more sample sources (such as reactor effluents) can be provided, for example, using macrofluidic connector ports, such as connector ports 85 (e.g., ferrule connector ports) formed at least partially within base 80 (FIG. 2D).

Preferably, each of the detection cells 64 has at least a reflective surface (e.g., an IR reflective surface). Generally, it is contemplated that the reflective surface may be provided in any manner desired. For instance, the reflective surface may be provided as part of the detection cells 64, as part of the base member 80 or as part of separate components that are preferably located within the detection cells 64. In the embodiment shown in FIGS. 2A through 2D, at least one reflective surface is provided by the inner elongated side surface 72 of the detection cell 64 and additionally or alternatively a reflective end surface, such as the end portion 84 of the surface 82 of the base member 80. In the particular embodiment shown in FIGS. 2A through 2D, the reflective elongated side surface is provided by applying a coating 100 of IR reflective material to an internal side surface of a capillary tube 102 to form the elongated (e.g., tubular) structure 70 and, additionally, applying a reflective coating 106 to the base member 80. Generally, without regard to the particular embodiment, the reflective surface preferably reflects at least about 50% and preferably at least about 75% of the radiation of interest under the operating conditions of interest, more preferably at least about 90%, even more preferably at least about 95% and still more preferably at least about 98%, and most preferably at least about 99% of the radiation of interest under the operating conditions of interest. Preferably, in addition to having reflective properties for the radiation of interest, the reflective materials (whether such reflective materials are provided as the structure itself or as a coating on the structure) are also preferably chemically inert to the analyte of interest under the operating conditions of interest. Exemplary reflective materials suitable for providing the reflective surface (whether such reflective materials are provided as the structure itself or as a coating on the structure) include gold, silver, metal halides, combinations thereof or the like. Other metals or metal alloys can also be used as reflective materials; however, some common metals or metal alloys are less desirable because they are less reflective and/or are less universally chemically inert. Hence, in some embodiments, the reflective surfaces comprise metals or metal alloys that have a reflective surface (e.g., as described above) and are substantially chemically inert to the analyte of interest under the detection conditions of interest. In some more particular embodiments, the reflective materials include metal or metal alloys other than stainless steel or copper.

A particularly preferred reflective elongated side surface can be realized using a flexible capillary waveguide, such as a capillary having both an external coating and an internal coating. The external coating can provide enhanced durability and/or flexibility relative to the uncoated capillary, and can preferably also allow for operation under conditions that include a temperature of at least about 100° C., preferably at least about 200° C. Many polymeric coatings are known in the art that would be suitable for an external coating. The internal coating can provide for enhanced reflectance of the radiation of interest (e.g., enhanced reflectance of infrared radiation). Preferably, the internal coating can be effective for reflecting at least about 50% and preferably at least about 75% of the radiation of interest under the operating conditions of interest, more preferably at least about 90%, even more preferably at least about 95% and still more preferably at least about 98%, and most preferably at least about 99% of the radiation of interest under the operating conditions of interest. Commercially available waveguides, such as capillary waveguides, can also be characterized with regard to attenuation loss (% incident radiation attenuated in the waveguide), with attenuation loss of a particular waveguide being dependent upon the material and/or coating of the waveguide, the length, the strait-path length and the bend radius, among other factors. Preferably, the waveguides can be selected and configured in the detection system to have an attenuation loss of not more than about 50%, and preferably not more than about 25% under the operating conditions of interest (including with regard to the radiation of interest), more preferably not more than about 10%, even more preferably not more than about 5%, still more preferably not more than about 2% and most preferably not more than about 1% under the operating conditions of interest (including with regard to the radiation of interest). Metals, such as gold and silver, and metal halides such as gold halides and silver halides, and/or combinations (including multi-layer coatings) of the foregoing are known in the art that would be suitable for an internal reflective coating. The capillary itself can be of any material, but preferably is a compatible and/or inert material. Many materials known in the art, such as silica, would be suitable for the capillary material. In one embodiment, the flexible waveguide capillary can be a silica capillary having an external acrylate coating and a multi-layer internal coating comprising a silver coating (adjacent the silica capillary) and silver iodide coating (adjacent the silver coating, and exposed to the radiation) (Polymicro Technologies, Phoenix, Ariz.). The particular dimensions of the capillary waveguide are not narrowly critical to the invention. Generally, elongated detection cells of the invention can have an inside diameter ranging from about 10 μm to about 5 cm, preferably from about 10 μm to about 4 cm, and more preferably from about 10 μm to about 2 cm. Generally, elongated detection cell waveguides can have substantially smaller inside diameters, such as ranging from about 10 μm to about 1 cm or from about 10 μm to about 5 mm. Particularly preferred waveguides, such as capillary waveguides can generally have an inside diameter ranging from about 10 μm to about 3.5 mm, preferably from about 40 μm to about 3 mm, from about 50 μm to about 2 mm, or from about 100 μm to about 1 mm. In one embodiment, a capillary waveguide of the invention can have an inside diameter of about 750 μm and an outside diameter of about 1200 μm. For detection cells having non-circular cross sections, the hydraulic radius of such detection cells can be equivalent to the hydraulic radius of the aforementioned preferred detection cells in the stated ranges. Further, the length of the elongated detection cells such as capillary waveguides is not narrowly critical. The appropriate length can be selected, for example, based on the desired total volume for the detection cells, with consideration given for example to residence time, fluid sample flow rate, data sampling times, etc. As one example, for a capillary waveguide having an inside diameter of about 100 μm to about 1 mm, the detection cell can have a length ranging from about 1 cm to about 100 cm, preferably from about 4 cm to about 40 cm, and in one embodiment can be about 10 cm. For many applications, relatively small volume detection cells are desirable, for example, with respect to obtaining faster response times and for integration with massively parallel microreactors.

Preferably, the samples 16 from the sample source (e.g. the reactor 26) respectively flow through the inlet 88 of the reaction cell 64 into and through the detection cavity 74 and are discharged from the reaction cell 64 through the outlet 92. The flow of the samples 16 through the reaction cells 64 may be intermittent, but is preferably substantially continuous over a period of time. During such flow, the samples 16, which are preferably reaction product streams, may change composition, concentration, or any number of other characteristics. Alternatively, those characteristics may stay substantially constant during flow through the cells 64.

In instances where a reactor is employed as the sample source, the samples may be provided as entire reaction effluents or as portion of reactor effluents depending upon the quantity of reaction product being produced. Where only a portion of the effluents are directed to the detection cells 64, it is preferable that the fluid distribution system 56 have one or more purge streams for removing extra effluent.

Also, during flow of the samples 16, the energy source 14 provides energy (represented schematically as 112) to the detection cells 64. Preferably, the energy source 14 can provide modulated IR radiation to the detection cavity 74 of each of the detection cells 64. While in the cavity 74, the IR radiation interacts with the samples 16 preferably both before and after the radiation reflects off of the reflective surface. Some of the radiation is absorbed by the samples 16 and the remainder of the radiation is reflected out of the detection cells 64 as reflected radiation that has interacted with the sample or a component thereof (such radiation being represented schematically as 122). Preferably, the reflected radiation is emitted from the detection cell 64 in a direction that is at least partially and more preferably substantially entirely opposite a direction that the initial radiation entered the cell 64.

The energy source 14 of the system 10 preferably includes a radiation source and radiation processing or encoding equipment (e.g., an interferometer). However, it is contemplated that other energy sources may be employed in the present invention. A typical radiation source is a glowbar or some other heated material capable of producing a polychromatic spectrum covering the infrared region of interest.

In the system 10 illustrated, the energy source 64 produces radiation 108 that is rendered parallel by a collimator end is passed on to a beamsplitter 110. The bearusplitter 110 then splits the radiation into two beams 112, 114, one of which beam 112 provides radiation to the samples 16 and one of which beam 114 is merely dumped as excess (i.e., unused) radiation. Preferably, in one approach, the radiation source provides abroad band IR spectrum of multiple wavelengths that is modulated by the interferometer in a signal frequency that is detectable by the detector 22. For further discussiors on radiation sources and interferomerers, particularly for use in IR spectroscopy, reference maybe bad to U.S. Pat. No. 6,541,271, which is hereby incorporated by reference for all purposes.

For interacting with the samples 16, the radiation leaves the beamsplitter 110 and enters the detection cavity 74 of each of the detection cells 64. Preferably, the radiation passes through a window 120 (e.g. an IR transparent window) prior to entering the detection cells 64, although not required. Inside the detection cells 64, a substantial portion (e.g., greater than 90%) of the radiation is reflected off of the reflective surface (e.g., the reflective end-surface and/or the reflective side surface), and particularly with respect to the reflective side surface, is preferably reflected off of the reflective surface multiple times, thereby producing reflected radiation 122 that passes through and interacts with the samples 16. As the radiation passes through the samples 16, certain constituents of the samples 16 will typically absorb various wavelengths of the reflected radiation, creating a sample-interacted radiation stream 122 that can provide a signature or spectra particular for an analyte of interest.

Advantageously, since the detection cell 64 operates in reflectance mode and reflects the reflected radiation through the samples 16 multiple times, the samples 16 have ample opportunity to absorb the various wavelengths of the radiation. Moreover, the detection cells 64 exhibit less radiation or signal loss since the reflective surfaces of the cells 64 limit or minimize radiation absorption. Because of these factors, the reflected radiation can provide a spectrum more indicative of characteristics, composition or concentration of the samples 16 or constituents within the samples 16 as opposed to non-reflected radiation.

The reflected (sample-interacted) radiation 122, upon leaving the detection cells 64, travels to the detector 22 of the detection system 20. A variety of suitable detectors may be employed in the present invention as long as the detector is capable of detecting the energy (e.g., reflected radiation 122) provided by the energy source 14. Typically, the detector will include an imaging device (e.g., a camera) and an energy processing device (e.g., optics configured for focusing energy such as light upon the camera).

Generally, it is preferable for the detector 22 to include a camera having the ability to create images based upon the reflected radiation from the detection cells 64. In one embodiment, it is contemplated that a bandpass filter may be employed to allow particular radiation to pass through the filter to a camera. In this instance, it is preferably for the energy source to be a broadband IR source, although not required.

In the preferred embodiments illustrated, the detector 22 includes an IR imaging camera 130 fitted with a focal plane array 132 (FPA) (e.g., a Mercury-Cadmium-Telluride detector or an Indium-Antimony detecor). The detector 22 also includes suitable collection optics 134 (e.g., one or more lenses) for focusing the IR reflected radiation 122 from the detection cells 64. In operation, the infrared camera 130 captures position sensitive infrared profiles sequentially in time at a rate (e.g. 60 frames/sec) that is typically determined by the frequency or speed of the interferometer motion. The sequential intensity profiles are transformed (using Fourier transformation) into a complete infrared spectrum with the aid of the processor 24. Thus, according to a preferred embodiment, the detector 22 provides parallel measurement of the infrared spectra of the samples 16 in a manner suitable for performing analysis on the samples 16.

The FPA 132 of the detector 22 preferably has a high signal to noise ratio to measure the signal coming from each sample in the library. Since the camera 130 is typically purchased as a finished package, the sensitivity of the FPA may be determined by the capabilities of the finished package, however, the overall sensitivity of the detection system 20 will be determined by the detector 22 (the camera, the FPA, electronics, filtering, etc.) and the rest of the screening apparatus.

In order to track sample characteristic changes (e.g., changes in concentration or composition) caused by chemical reactions or other factors over time, the IR spectrum of each of the samples 16 is preferably captured at multiple time intervals as the samples 16 flow through the detection cells 64. As an example, the IR spectrum may be captured at time intervals of 20 seconds or smaller. Accordingly, if the time intervals are short, it is preferable to employ a high speed IR Camera for capturing the spectra.

Figure 3A:
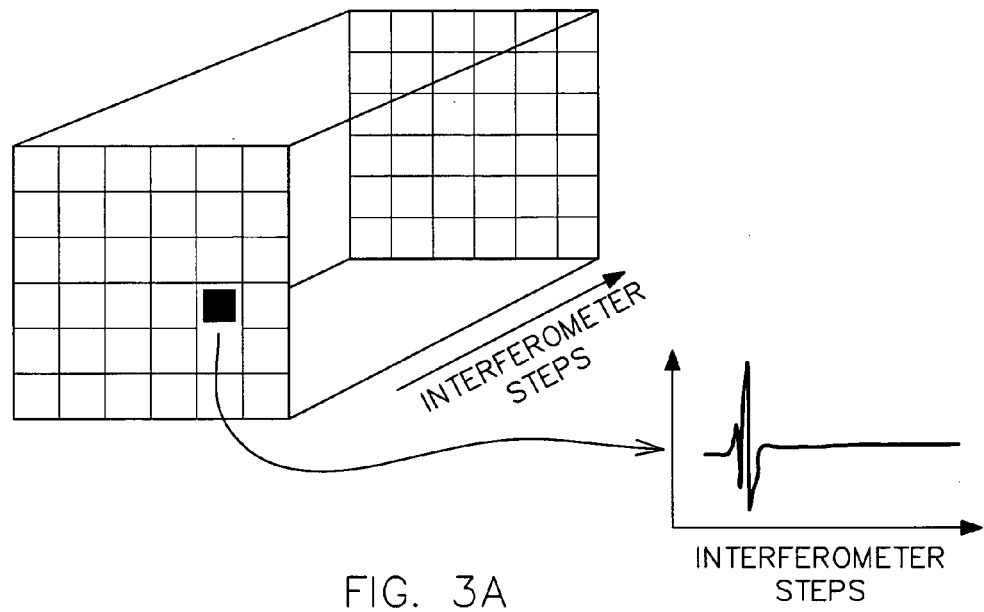
FIGS. 3A and 3B are schematic and graphical representations of data typical of that resulting from samples screened according to aspects of the present invention.
Figures 4A, 4B:
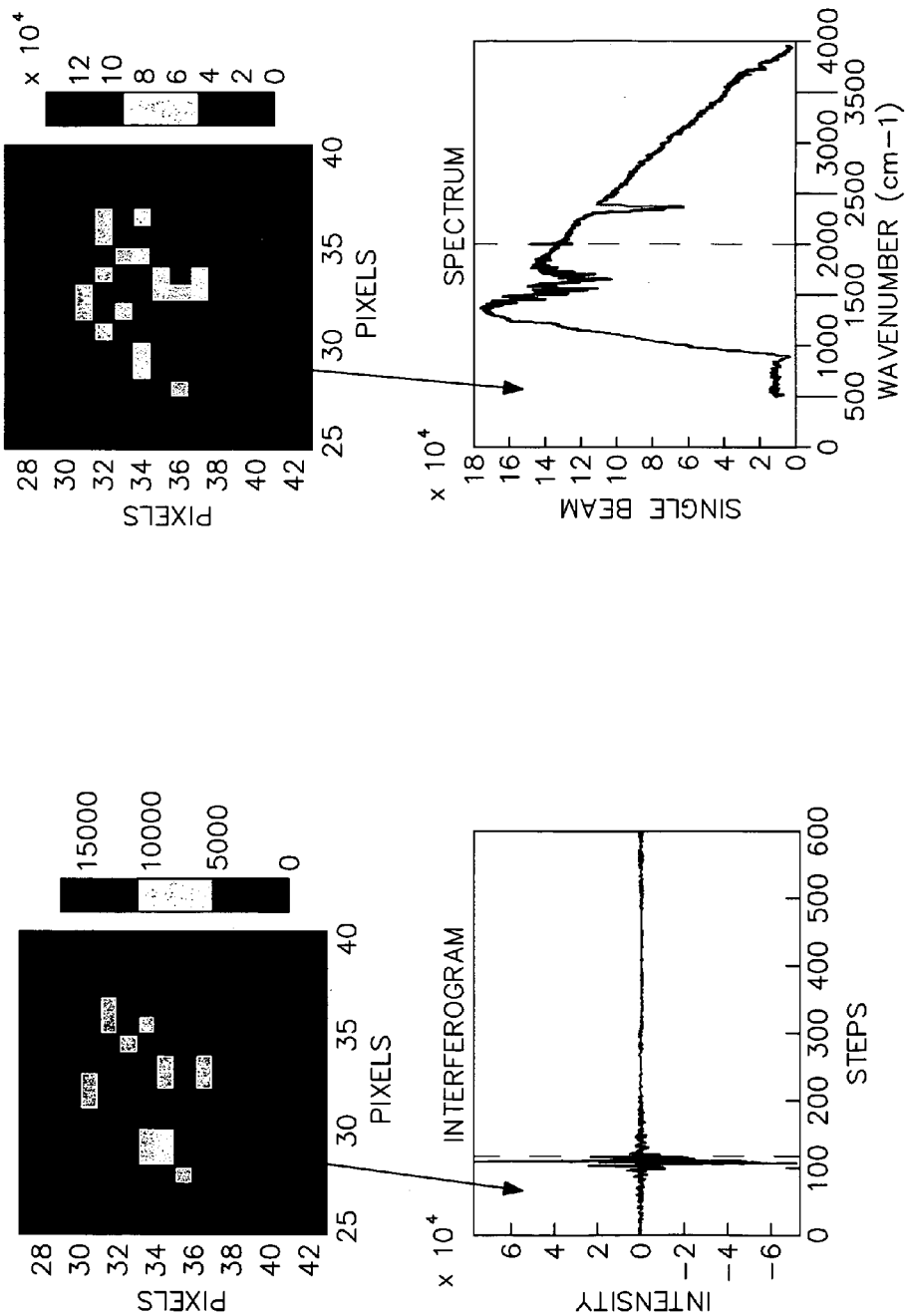
FIGS. 4A and 4B are graphical representations of data resulting from samples tested according to aspects of the present invention.

Preferably, the images captured by the IR camera 120 are collected to create a series of points on an interferogram taken over a period of time for each sample 16. Although the true time required to obtain the series of points relies on the data acquisition rate and on the computer processing, the ability of the IR camera 130 to operate at higher rates (e.g., faster than 120 frames/sec) can allow for more points to be taken over the period of time such that the points provide a more informative analytical tool for analyzing the samples. Referring to FIGS. 4A and 4B, there is illustrated an example of an interferogram according to the present invention and, referring to FIG. 3A, there is illustrated an image cube for organizing the points of the interferogram, as interferometer steps.

Figure 3B:
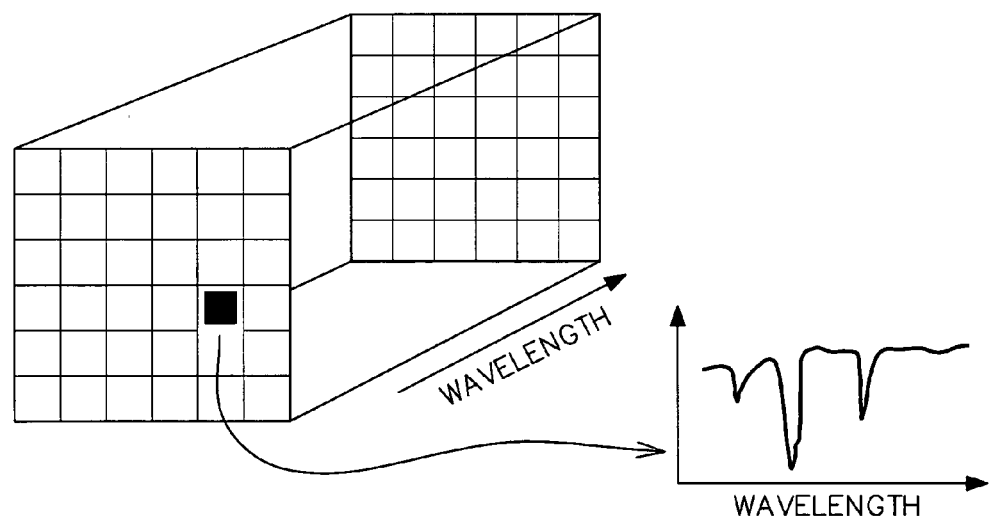

For analysis of the samples 16, the points of the interferogram can be transformed back to a more useful spectrum showing intensity versus wavelength with the aide of a Fourier transform performed by the processor 24. Referring to FIG. 4B, there is illustrated such a spectrum representation that resulted from the transformation of the interferogram of FIG. 4A. Also, referring to FIG. 3B, there is illustrated an image cube of such intensity versus wavelength representations that resulted from the transformation of the points of the interferogram of the image cube of FIG. 3A.

In order to perform the Fourier transform, the processor 24 will typically correspond the time of the image taken by the camera 130 with factors (e.g., mirror position) of the interferometer of the IR radiation source. Thus, it is preferable for the interferometer to have an electronic trigger for triggering the camera shutter to allow correspondence between the position of the interferometer and the time at which an image was captured. In this way, a series of plots of absorbance versus wavelength can be constructed for every sample. In one embodiment, the processor 24 (FIG. 1) can be in electrical communication with and can have cooperative control over both the detection system 20 (e.g., including for example the detector 22) and the energy source 14 (e.g., including for example the interferometer).

Data processing may include multiple steps, especially in preferred embodiments in which, as discussed above, a detection system comprises a focal plane array (or other imaging device) in which the focal plane array (or other imaging device) and a particular corresponding detection cell are configured so that multiple pixels (preferably at least four pixels) of the focal plane array (or the other imaging device) receive radiation from the corresponding detection cell. For example, the intensity of the absorption spectra at each pixel can be analyzed for a specific analyte peak (e.g., corresponding to a particular wavelength) by first performing a baseline correction and then integrating the peak over a range that includes the peak. The integrated peak area for each of the pixels corresponding to a particular detection cell (i.e., to a particular capillary waveguide in this experiment) can then be further processed (e.g., summed or averaged or otherwise statistically manipulated) to generate one or more representative combined data points for the analyte of interest for that particular detection cell. Moreover, such pixel integration and such processing of pixel data for pixels corresponding to a particular detection cell can be repeated more than one time, for example, for each of a series of measurement periods taken on a particular sample in a particular detection cell, to generate multiple representative combined data points for each detection cell (e.g., each corresponding to measurements taken during a different discrete time period). These multiple representative combined data points can themselves be further processed (e.g., summed or averaged or otherwise statistically manipulated) to generate a representative data point for the analyte of interest for that particular detection cell that is both spatially processed (e.g., integrated re multiple pixels per detection cell) and temporally processed (e.g., integrated re multiple measurements at multiple discrete times). Such data processing can be preferably effected using a computer program (e.g., written in software such as MATLAB software according to methods known in the art) and a microprocessor. Likewise, the resulting data, including both raw data and processed data, can be represented graphically according to methods and using software known in the art.

Also, in operation, it may be preferable to independently calibrate each detection cell. Without being bound by theory, each detection cell and/or each component thereof (e.g., each capillary waveguide) can have variations (e.g., manufacturing variations), for example with regard to the condition of the reflective surface, etc., that can affect the calibration for that particular detection cell. Hence, although a calibration universally applicable to two or more detection cells may be desirable and feasible for some applications, it is generally preferably to develop separate calibration curves for each detection channel of the detection system, and to process the data from a particular detection channel using the corresponding calibration curve for that particular detection channel. It is also generally preferable to develop calibration data for each analyte of interest in a particular set of experiments.

Reactants and reaction products suitably handled by the system 10 of the present invention can vary across a wide spectrum. Thus, samples provided to the detection system may be provided by gas phase reactions, catalyst reactions or the like. Moreover, other processes such as evaporation may produce the samples. Alternatively, the samples may be non-synthesized or non-artificially-processed samples such as air samples.

Although the various aspects of the invention have been described above in connection with the particular embodiments depicted in FIG. 1, FIGS. 2A through 2D, FIGS. 3A and 3B and FIGS. 4A and 4B, it should be understood that such various aspects are generally applicable, alone and in various combinations, and in particular, are not limited to the particular embodiments with which they are described.

As discussed, formation and integration of the detection cells of the present invention may be accomplished according to a variety of techniques. Referring to FIGS. 5A-5F, embodiment-specific reference numerals are shown therein, with corresponding reference numerals from FIGS. 1 and 2A through 2D included parenthetically in the following description. Hence, although embodiment-specific reference numerals are shown in connection with these figures, it is to be understood that the general descriptions and characterizations relating to the corresponding parenthetical reference numerals are applicable to the embodiments shown in these FIGS. 5A through 5E. There is illustrated therein the formation of one detection cell unit 200 (66) having a plurality of detection cells 202 (64). It should be understood that the detection cell 202 (64) is illustrated for exemplary purposes only and is not intended to limit the present invention. Moreover the detection cells 202 (64) may be employed in any of the various embodiments of systems or apparatus or methods discussed herein and can particularly be employed in the system 10 of FIG. 1. As such, it should be understood that the detection cells 202 (64) operate as previously described.

Figure 5A:
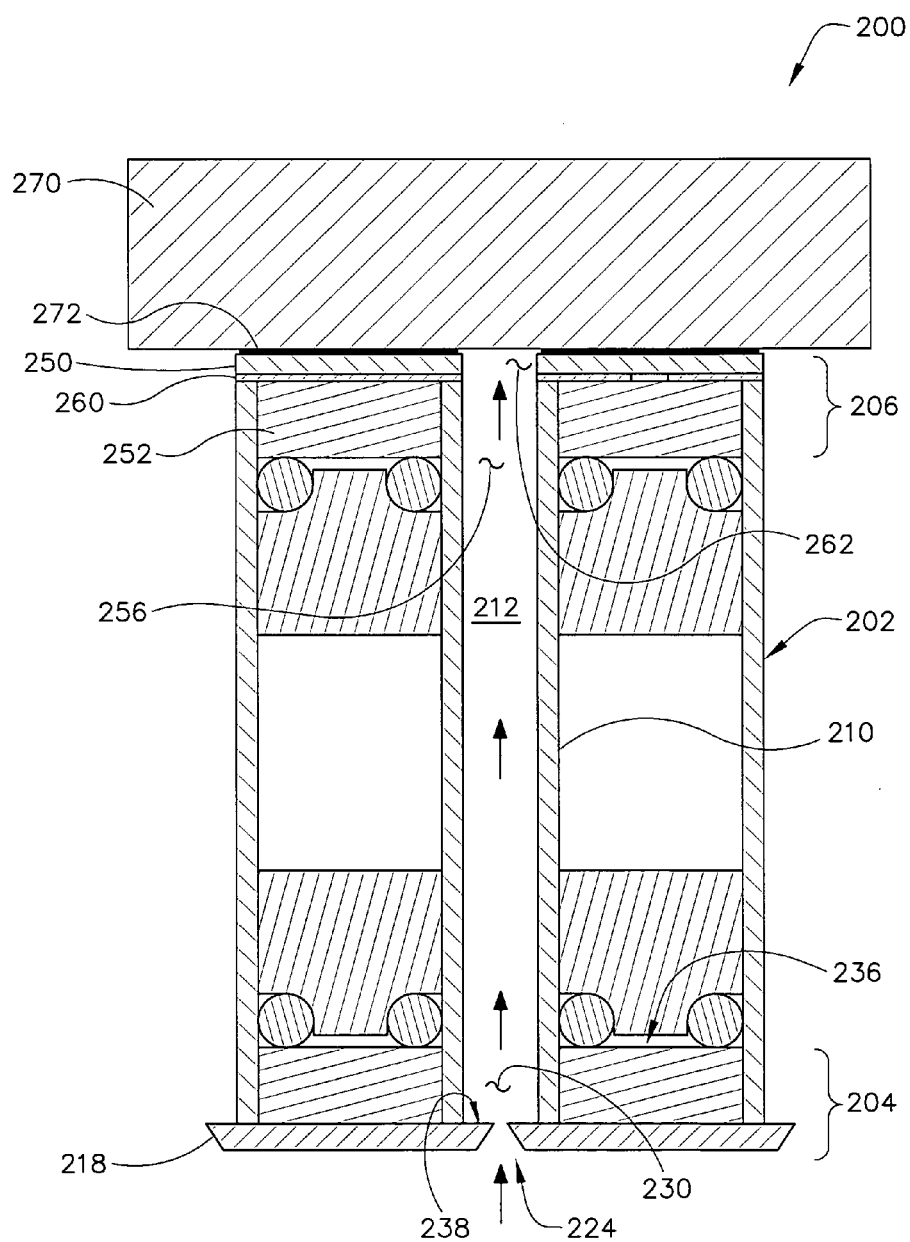
FIGS. 5A-5F illustrate one embodiment of a detection cell unit and its formation according to an aspect of the present invention, including a cross-sectional view of one detection cell of a detection cell unit (FIG. 5A), a schematic cross-sectional view showing, in enlarged form, details of the base member and the manifold member of the detection cell unit (FIG. 5B), a top plan view of a silicon wafer used in fabrication of the base member, showing a photolithographic pattern thereon (FIG. 5C), a top plan view of a glass wafer used in fabrication of the base member, showing an ultrasonic machining pattern for forming throughholes, thereon (FIG. 5D), a top plan view of a silicon wafer used in fabrication of the manifold member, showing a pattern of channels and throughholes thereon (FIG. 5E), and a top plan view of the opposite side of the silicon wafer of FIG. 5E, showing a photolithographic pattern thereon (FIG. 5F).

With reference to FIG. 5A, there is illustrated a portion of the detection cell unit 200 (66) sufficient to illustrate at one full detection cell 202 (64). It shall be understood however, that the detection cell unit 200 (66) may include as many or as few detection cells 202 (64) as desired (e.g., 2, 4, 8, 16, 48 or more cells). The detection cell unit 200 includes a base member 204 and a manifold member 206 (e.g., an exhaust manifold) and elongated (e.g., tubular) structures 210 (70) (e.g., waveguides) extending therebetween for forming the detection cells 202 (64) and defining detection cavities 212 (74) within the detection cells 202 (64). The elongated (e.g., tubular) structure 210 (70) is preferably substantially identical or similar to the structure 70 of FIGS. 1 and 2A.

Figures 5B, 5C:
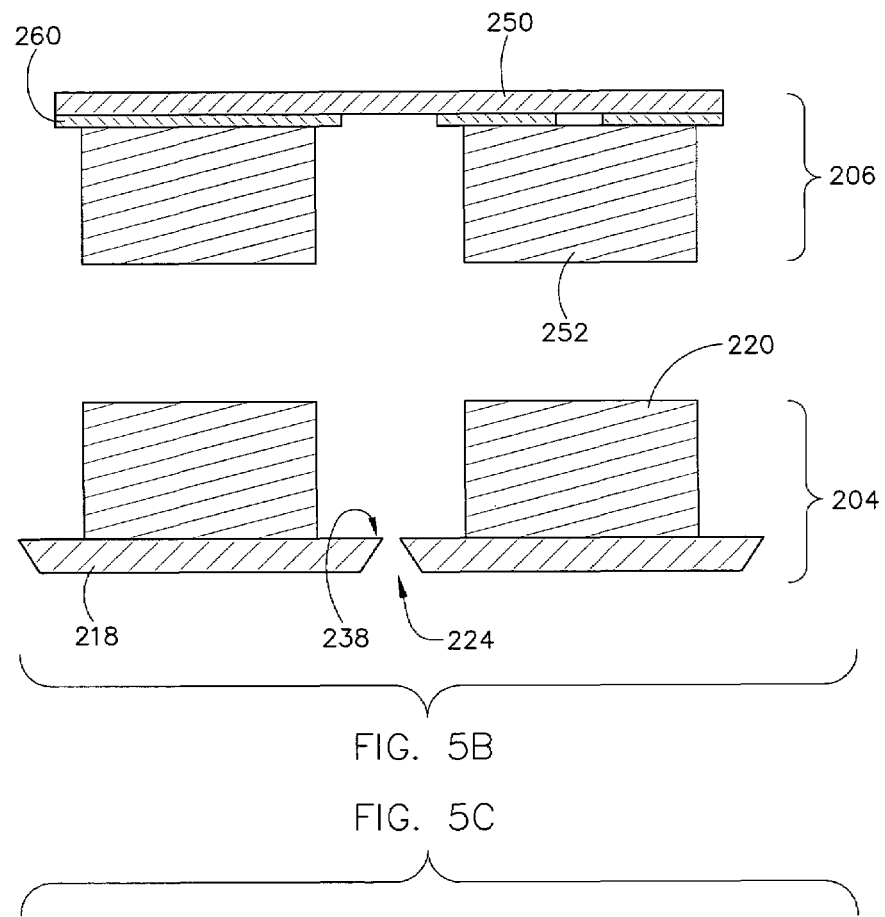
Figure 5D:
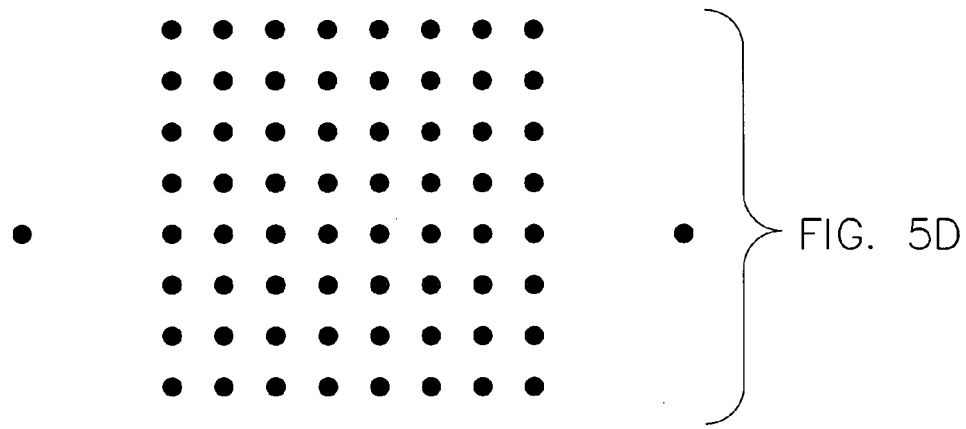
Figure 5E:
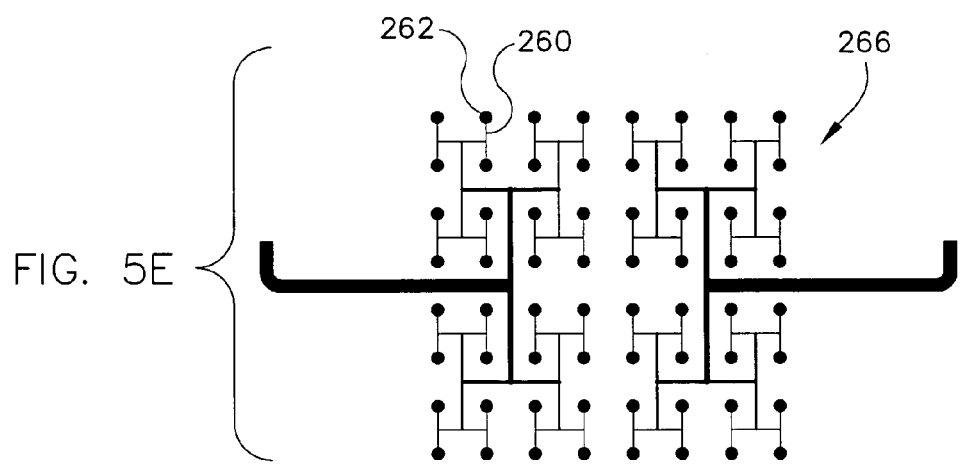
Figure 5F:
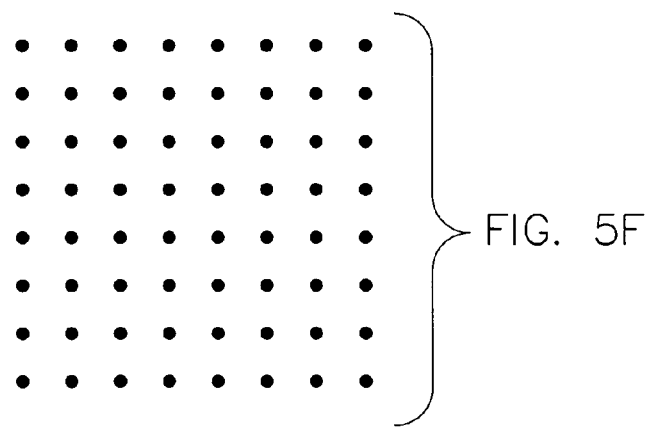

The base member 204 is formed from a silicon wafer 218 and a glass wafer 220. For forming the base member 204, the silicon wafer 218 is processed to provide an inlet 224 (88) (e.g., through-holes) in the silicon wafer 218 for each of the detection cells 202 (64). In one particular embodiment, the inlets 224 (88) are formed by a multi-step process. First a 2000 angstrom low stress LPCVD silicon nitride is deposited on an R-primed, P-doped, double sided polished silicon wafer. Then, 1.6 um photolithography is carried out on a front side of the wafer in a pattern as illustrated in FIG. 5C. The photolithographic pattern is transferred on the silicon nitride layer by a plasma silicon nitride dry etch process. Thereafter, the inlets 224 (88) are formed in the wafer 218 using a potassium hydroxide (KOH) silicon etch. Finally, the silicon nitride layer is removed by a phosphoric acid wet etch. It should be understood that this inlet forming process is presented for purposes of example only and that various other processes may also be employed.

Preferably, the inlets 224 (88) in the silicon wafer have a larger cross sectional area at a side interfacing a sample source and the cross section is quadratically decreased as the inlets 224 (88) approach the cavities 212 (74) of the cells 202 (64). In this manner, the cross sectional area of the inlet 224 (88) is decreased to only a fraction of that for the internal cross sectional area of the cavity 212 (74) of the tubular structure 210 (70).

Openings 230 (e.g., through-holes) for receiving the tubular structures 210 are formed in the glass wafer 220. In particular, the openings 230 are formed in the glass wafer 220 by ultrasonic machining the openings 230 in the pattern shown in FIG. 5D.

Formation of the base member 204 is accomplished by attaching the silicon wafer 218 to the glass wafer 220. Preferably, the silicon wafer 218 is attached to the glass wafer 220 by anodic bonding. Moreover, it is preferable for the openings 230 of the glass wafer 220 to align with the inlets 224 of the silicon wafer 218 upon attachment to each other.

The base member 204 is typically coated with one or more materials and particularly with a reflective material. In one preferred embodiment, at least one surface of the base member 204 is coated (e.g., by sputtering) by a layer of Chromium approximately 20 nanometers thick. In the embodiment shown, such surface is provided by an exposed surface 236 of the glass wafer 220 and by portions of a surface 238 of the silicon wafer 218 that are exposed by the openings 230 of the glass wafer 220. Thereafter, in the preferred embodiment, the portions of the surface 238 of the silicon wafer 218 are additionally coated (e.g., by sputtering) by a layer of gold for forming an infrared radiation reflective end surface (84).

The manifold member 206 is also formed of a silicon wafer 250 (e.g., a silicon on insulator wafer or the like) that is attached (e.g. by anodic bonding) to a glass wafer 252. The glass wafer 252 is formed with openings 256 substantially corresponding to the openings 230 of the glass member 220 of the base member 204 and such openings 256 may be formed using similar or same techniques. The silicon wafer 250, however, is formed with a pattern of channels 260 and through-holes 262 such as the pattern 266 shown in FIG. 5E, which can operate as outlets (92).

The particular pattern illustrated was formed on the silicon wafer 250 by performing 10 μm photolithography with a mask on the wafer using a 100 μm device and 400 μm handle thickness. The photolithographic pattern is transferred to the wafer 250 by use of advanced silicon etch. Additionally, an opposite side of the wafer 250 is etched using 10 μm photolithography with the pattern of FIG. 5F for completing the through-holes 262 of the wafer 250. Of course, the skilled artisan will recognize that various alternative techniques may be used to form such a pattern.

The detection cell unit 200 (66) is formed by inserting the ends of the elongated (e.g., tubular) structure 210 (70) respectively into the openings 230, 256 of the glass wafers 220, 252 and attaching them therein. Such attachment may be accomplished by anodic bonding to the silicon wafers 218, 250 or otherwise.

In the embodiment of FIG. 5A an IR transparent window 270 (120) has been placed in substantially coextensive relationship with the manifold member 206 and has been sealed thereto with a sealing material 272. In this manner, samples flowing through the detection cells 202 (64) are forced to exit the detection unit 200 (66) through the channels 260 (operating as outlet ports 92) formed in the manifold member 206. In an alternative embodiment, however, and referring to FIG. 6, it is also contemplated that a silicon wafer 280 without the through-holes 262 of the wafer 250 of FIG. 5A could also be employed for the same purpose.

Figure 6:
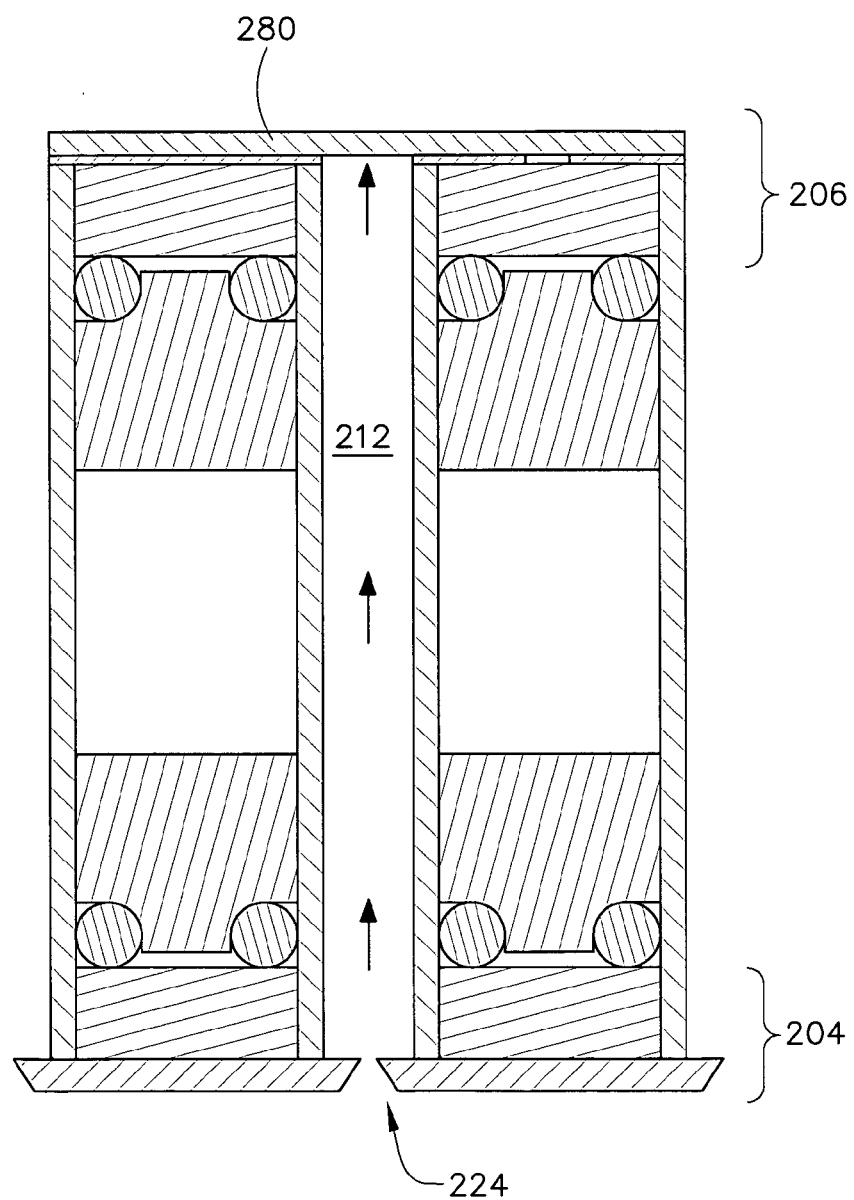
FIG. 6 illustrates another embodiment of a detection cell unit alternative to that shown in FIG. 5, as a cross-sectional view of one detection cell of a detection cell unit.

Depending upon the materials used for the detection cells, it may be advisable to employ one or more seals for assisting in maintaining the proper flow of the samples through the detection cells. As shown in FIGS. 2C and 2D, for example, base seal 330 is provided for sealing the elongated tubular structures 70 (e.g., capillary waveguides 102) to the base 80 for adaptation to a macrofluidic supply (from sample sources) and for isolation of adjacent detection cells 74. As shown in FIGS. 5A and 6, for example, plates 286 and O-rings 288 have been employed to assist in sealing between the elongated (e.g., tubular) structures 210 (70) and the base or manifold members 204, 206. Generally, the seals can be effective for the operating conditions (e.g., temperature, pressure) to which the detection cells will be exposed. The seals can therefore be any suitable material, and in general, are preferably a deformable material. Particular materials that can be used for such seals include for example, silicone, Teflon® and graphite, and in embodiments using ferrules, for example, also PEEK, polyamide and/or stainless steel or other metals. The seals can generally be separate individual seals (e.g., separate o-rings), or can be a common integral seal (e.g., a common gasket sheet), and in any event, can generally in any suitable shape, such as a gasket having apertures, or a ring seal, such as an o-ring seal.

Figure 7A:
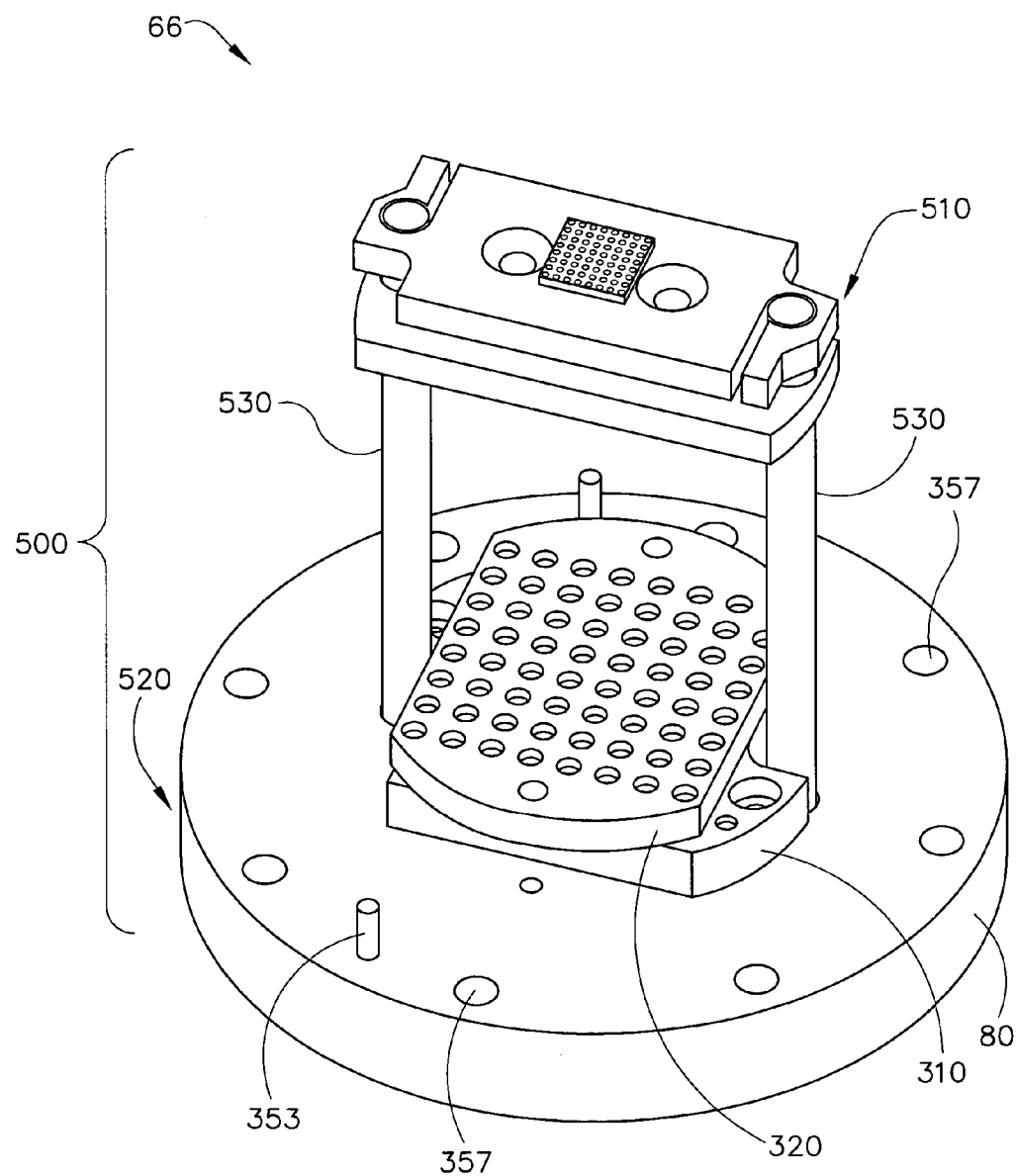
FIGS. 7A through 7C illustrate another alternative detection cell unit, configured to have sixty-four detection cells substantially according to the design of FIGS. 2C and 2D, and adapted for high-pressure and high-temperature operation, including a perspective view of a detection cell support structure (FIG. 7A), a perspective view of a cross-section of the base structure of the support structure (FIG. 7B), and a perspective view of the integral pressure chamber of the detection cell unit (FIG. 7C).
Figure 7B:
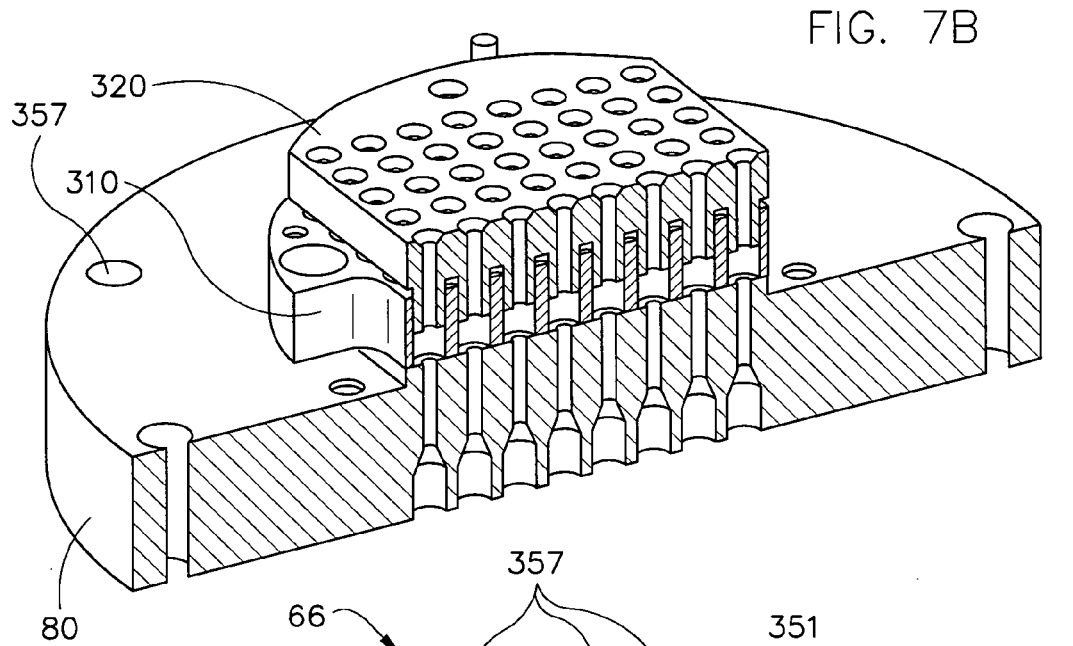
Figure 7C:
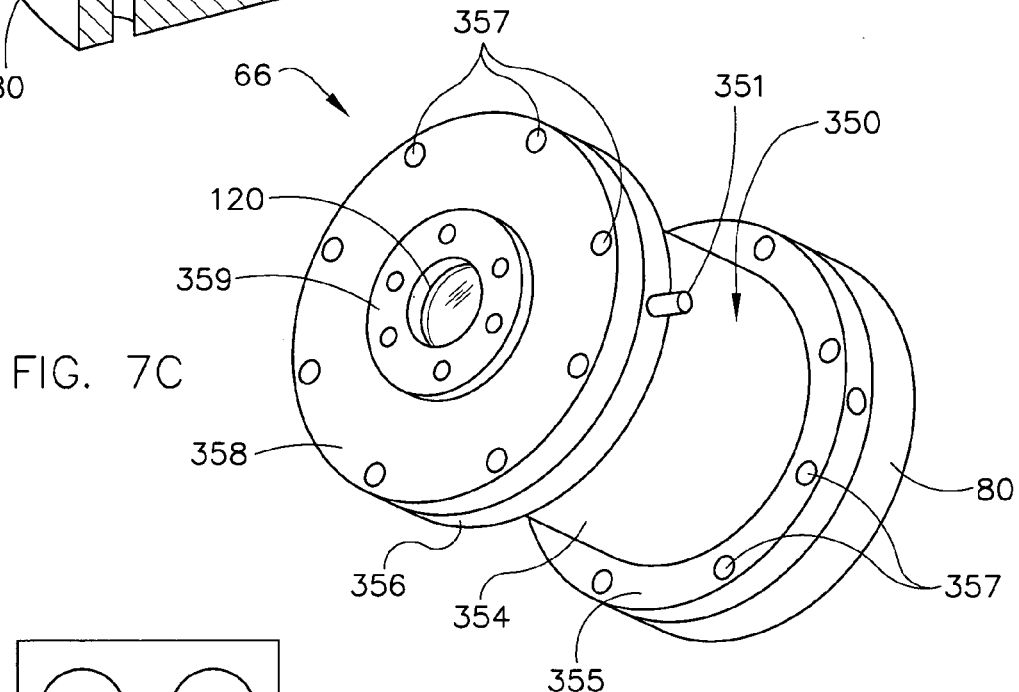

Referring to FIGS. 7A through 7C, there is illustrated therein a support structure for the formation of an alternative detection cell unit 66 having a plurality of detection cells 64. Preferably, each of the detection cells 64 can be of a design as described in connection with FIG. 1 and FIGS. 2C and 2D. It should be understood, however, that the detection cell 64 is illustrated for exemplary purposes only and is not intended to limit the present invention. Moreover this detection cell unit 66 and the detection cells 64 may be employed in any of the various embodiments of systems or apparatus or methods discussed herein and can particularly be employed in the system 10 of FIG. 1. As such, it should be understood that the detection cells 64 can operate as previously described. Also, although illustrated as sixty-four detection cells 64 in an 8×8 array configuration, it is to be understood that the detection cell unit 66 may include as many or as few detection cells 64 as desired (e.g., 2, 4, 8, 16, 48, 64, 96, 128, 156, 192 or more cells), and may be relatively positioned in any type of configuration.

With reference to FIG. 7A (and with further reference to FIGS. 2C, 2D and associated description thereof) a detection cell unit 66 comprising two or more detection cells 64 can be formed in a support structure, generally indicated as support frame 500. The support frame 500 can comprise an upper support block 510, a lower support block 520 and one or more, preferably two or more support stantions 530 providing a structural connection between the upper support block 510 and the lower support block 520. The lower support block 520 can support a first end 71 of an elongated structure 70 (preferably a capillary waveguide 102), (not shown in FIG. 7A), and can comprise, for example, a base 80, a first seal plate 310 and a second seal plate 320, as described in detail in connection with FIGS. 2C and 2D, as shown in further detail in connection with FIG. 7B. The upper support block can support and align a second end 73 of an elongated structure 70 (preferably a capillary waveguide 102), (not shown in FIG. 7A), and can comprise, for example, a single monolithic block, or multiple plates (as shown), optionally including a gasket material or other deformable material between such multiple plates (e.g., having apertures to accommodate the detection cells passing therethrough) for supporting the detection cells. The first ends 71 of the elongated structures 70 (preferably capillary waveguides 102) can be installed into the lower support structure 520 and isolated from each other by sealing as described in connection with FIGS. 2C and 2D. Likewise, the second ends 73 of the elongated structures 70 (preferably capillary waveguides 102) can be installed into the upper support structure 510, such the second ends 73 are held in a spaced relationship to the inner surface of the radiation-transparent window 120 (not shown in FIG. 7A), thereby forming a gap that can operate as an outlet port 92 (see FIG. 2C and FIG. 2D) for each of the detection cells 64.

Referring now to FIG. 7C, the detection unit 66 of FIGS. 7A and 7B (as described above) can further comprise a common effluent chamber (e.g., common pressure chamber 350, as shown). A sweep gas inlet port 351 adaptable for fluid communication with a sweep gas source can be provided for admitting a sweep gas into the common effluent chamber (e.g., pressure chamber 350), and a sweep gas outlet port 352 (not shown in FIG. 7C) can be provided for discharging the sweep gas out of the common effluent chamber (e.g., pressure chamber 350). The base 80 of the lower support block 520 can be effectively used to form the pressure-chamber base 80 of the common effluent chamber (e.g., common pressure chamber 350). The common effluent chamber (e.g., common pressure chamber 350) can be formed from other components in combination with the pressure-chamber base 80, including for example one or more pressure-chamber walls 354 (illustrated in FIG. 7C as a cylindrical pressure-chamber wall 354) having a lower first flange 355 and an upper second flange 356, and a pressure-chamber cap 358. For example, the pressure-chamber base 80 can be sealingly enaged with the pressure-chamber wall 354 by providing a sealing material (e.g., gasket) between the lower surface of the first flange 355 and the upper peripheral surface of the base 80 and fixedly securing the first flange 355 to the pressure-chamber base 80 (e.g., using a suitable fastener such as one or more bolts or clamp or hydraulic press, etc.). Likewise, for example, the pressure-chamber cap 358 can be sealingly enaged with the pressure-chamber wall 354 by providing a sealing material (e.g., gasket) between the upper surface of the second flange 356 and the lower peripheral surface of the pressure-chamber cap 358 and fixedly securing the first flange 355 to the base 80 (e.g., using a suitable fastener such as one or more bolts (e.g., through through-holes 357) or clamp or hydraulic press, etc.). If desired, one or more alignment pins 353 can be used to align the various components of the pressure chamber 350 with each other. The pressure-chamber cap 358 can further comprise a radiation-transparent-window support 359 adapted both to sealingly engage and support the radiation transparent window 120 and to sealingly engage and/or be disposed upon and/or integrated with the pressure-chamber cap 358.

Generally, the detection system, comprising a detection cell unit 66, for example, such as that described in connection with FIGS. 2C, 2D, 7A, 7B and 7C, can be operated in a number of applications. For example, the detection system can be advantageously used in combination with a parallel reactor for evaluating reaction chemistries, such as catalysts, or reaction conditions suitable for a particular reaction of interest—including both discovery phase research and optimization research. See, for example, Example 2. The detection system can also be used in other types of research endeavors, such as for example, in adsorption/desorption studies. For example, the the two or more detection cells of the detection system can be in fluid communication (direct, continuous and/or indirect isolatable fluid communication) with two or more adsorption/desorption vessels. The detection system of the invention can likewise be used in other applications, such as quality control or quality analysis applications, or such as process monitoring and/or process control applications.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The following examples illustrate the principles and advantages of the invention.

EXAMPLE 1

A reactor engineering experiment was performed using a high-pressure/high-temperature detection unit having sixteen detection channels, configured substantially as described in connection with FIGS. 2C, 2D, 7A, 7B and 7C, and set-up in a detection system substantially as described in connection with FIG. 1, to evaluate cross-talk between adjacent detection cells. Each of the detection channels of the detection system included both a reflective end surface realized as a gold-plated end surface, and an elongated reflective side surface realized as a flexible capillary waveguide comprising a silica capillary having an acrylate external coating and a Ag/AgI internal coating.

Sixteen (16) capillary waveguides (Polymicro Technologies, Inc. Phoenix, Ariz., Part No. HWEA1200750), each 10 cm long, were installed in a rectangular 4×4 array configuration into a support structure substantially as described in connection with FIG. 7A to form a detection unit comprising sixteen isolated detection cells. Crosstalk experiments were performed to evaluate seal integrity. Briefly, eight (8) detection cell channels selected in a checkerboard pattern were effused with a gas containing 5% ethylene/95% nitrogen (by mole, based on partial pressure) from a common gas source via a common mass-flow-controller (MFC) (Celerity Group, Inc. Milpitas, Calif.). The remaining eight (8) detection cell channels were effused with dry nitrogen via a second MFC (Celerity Group, Inc. Milpitas, Calif.). The detection unit comprising the array of sixteen waveguide detection cells was placed in the optical path (as previously described) of an infrared (IR) interferometer from Nicolet Instruments Co. (Madison, Wis., Model No. Nexus 870) operating in step-scan mode. The detector for Fourier-Transform Infrared (FTIR) imaging was a 64×64 element (4096 total pixels) mercury-cadmium-telluride (MCT) focal plane array (Santa Barbara Focal Plane, Inc., Santa Barbara, Calif.).

Figure 10:
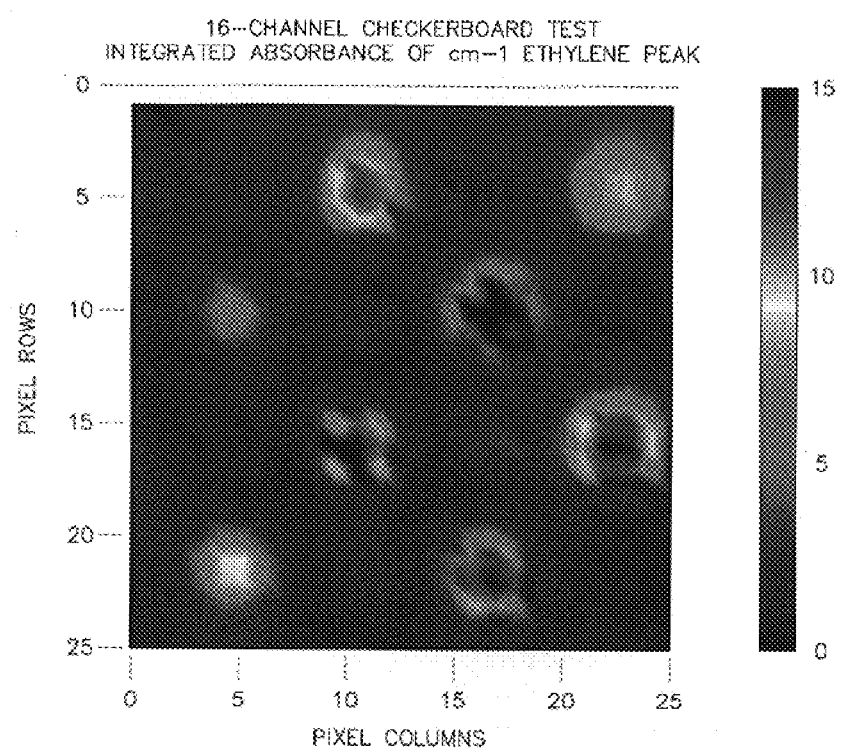
FIG. 10 shows the experimental data resulting from a reactor experiment evaluating the degree of cross-talk between adjacent detection cavities, as discussed in Example 1, using a detection system configured substantially as described in connection with FIG. 1 and including a detection cell unit substantially as described in connection with FIGS. 2C, 2D and 7A through 7C.

A background image was taken flowing 3 sccm of dry nitrogen through each of the sixteen waveguide detection cells. Then, 5% ethylene/95% nitrogen flow was started at 3 sccm flow through each of eight waveguide detection cells in a checkerboard pattern, while 3 sccm dry nitrogen was continued through the other eight waveguide detection cells. The flow was allowed to equilibrate for ~30 minutes, and an image was taken using IsysAcquire software (Spectral Dimensions, Inc., Onley, Md.) which controls the spectrometer and detector operation. Using a MATLAB program, absorption spectra at each pixel were analyzed for a specific ethylene peak (at ~1400 1/cm) by first performing a baseline correction and then integrating the peak from 1400-1600 1/cm. FIG. 10 shows the integrated peak area (plotted as a color) on an x-y coordinate plane corresponding to pixel location, as determined by the MATLAB program. The integrated peak area for each of the pixels corresponding to a particular detection cell (i.e., to a particular capillary waveguide in this experiment) was summed, and the (uncalibrated) summation data is reported for each detection cell in Table 1. (Since, as noted generally above, it is preferably to independently calibrate each capillary waveguide, the variation in the reported values of Table 1 for the different detection cells can be attributed to the data being uncalibrated).

TABLE 1

| Row | Column | Known Gas Composition | Integrated Waveguide Ethylene Peak Area (AU/cm) |
|---|---|---|---|
| 1 | 1 | 100% Nitrogen | 28.5 |
| 1 | 2 | 95/5 Nitrogen/Ethylene | 146.5 |
| 1 | 3 | 100% Nitrogen | 29.6 |
| 1 | 4 | 95/5 Nitrogen/Ethylene | 131.1 |
| 2 | 1 | 95/5 Nitrogen/Ethylene | 53.3 |
| 2 | 2 | 100% Nitrogen | 19.5 |
| 2 | 3 | 95/5 Nitrogen/Ethylene | 212.3 |
| 2 | 4 | 100% Nitrogen | 17.7 |
| 3 | 1 | 100% Nitrogen | 17.8 |
| 3 | 2 | 95/5 Nitrogen/Ethylene | 141.8 |
| 3 | 3 | 100% Nitrogen | 31.5 |
| 3 | 4 | 95/5 Nitrogen/Ethylene | 193.1 |
| 4 | 1 | 95/5 Nitrogen/Ethylene | 114.6 |
| 4 | 2 | 100% Nitrogen | 29.4 |
| 4 | 3 | 95/5 Nitrogen/Ethylene | 153.8 |
| 4 | 4 | 100% Nitrogen | 10.9 |

The amount of crosstalk was determined by evaluating the summation of the integrated ethylene peak area in waveguides known to contain only dry nitrogen. This experiment demonstrated that the cross-talk of the detection unit was acceptable for the application of interest.

EXAMPLE 2

Six different candidate catalyst compositions, designated as Catalyst A through F, were screened for CO oxidation using a six-channel parallel fixed bed reactor and a parallel FTIR detection system. The catalysts A through D were supported mixed metal oxide catalysts prepared by incipient wetness impregnation of catalyst supports. Catalyst E was a commercially available catalyst used as a standard in this experiment. Each of Catalysts A through E had particle sizes between 180 and 425 um, and were diluted with SiC (180-425 um) 1:4 by volume. Catalyst F was a blank; the reaction vessel contained only the Si—C diluted catalyst support. The six-channel parallel fixed bed reactor was configured substantially as described in U.S. Pat. No. 6,149,882 to Guan et al., and included flow-through reaction vessels having a length of six inches and an inside diameter of 4 mm. The catalyst bed was 2 inches in height, and was positioned substantially in the middle of the reactor. The feed contained 67% $O_2$, 2% CO and 31% $N_2$; the total flow was 640 ml/min which corresponds with a space velocity of 50.000 $h^{-1}$. In this example, the six-channel parallel fixed bed reactor was a sample source of six discrete sample streams comprising reaction products and unreacted reactants from the six catalyzed reactions. The six samples were fed individually to a corresponding six detection channels of the detection system. The parallel FTIR detection system included a high-pressure/high-temperature detection unit having six detection channels, configured substantially as described in connection with FIGS. 2C, 2D, 7A, 7B and 7C, and set-up substantially as described in connection with FIG. 1. Each of the detection channels of the detection system included both a reflective end surface realized as a gold-plated end surface, and an elongated reflective side surface realized as a flexible capillary waveguide comprising a silica capillary having an acrylate external coating and a Ag/AgI internal coating. Hence, each of the six samples were fed to the inlet port of one of the detection channels of the detection system. Each of the six sample streams were irradiated with infrared radiation (from an FTIR spectrometer) within each respective detection channels. Samples were allowed to interact with reflected infrared radiation within their respective detection channels, such reflected radiation including both end-reflected radiation and side-reflected radiation. The samples were discharged from their respective detection cells into a common pressure chamber configured with a nitrogen sweep system, as described. The FTIR spectrometer was operated in step-scan mode at 8 $cm^{-1}$ spectral resolution, with 100 ms sampling time at each mirror step, for a total scan time of ~6 minutes. The optics were set for total reflectance off of the gold reflective end surface of each of the detection cells. The sample-interacted radiation was detected using a 64×64 element focal plane array, and the data processed using fast Fourier transformation (FFT), generally as described. The FFT of the interferogram was taken for each pixel of the focal plane array, and was compared to background scan (100% dry nitrogen) to obtain absorbance as a function of wavenumber or frequency. Data from pixels corresponding to a particular detection cell were co-added using a software program to increase the signal to noise ratio. The integrated area of both the CO and $CO_2$ peaks were determined after baseline correction. The areas of these peaks were converted to concentration using previously established calibration curves, with a separate dedicated calibration curve corresponding to each detection channel. The six-channel parallel evaluation experiment was performed four times, at four different reaction temperatures: 40° C., 100° C., 140° C. and 180° C.

Figure 8A:
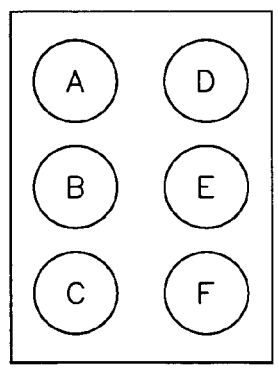
Figure 8B:
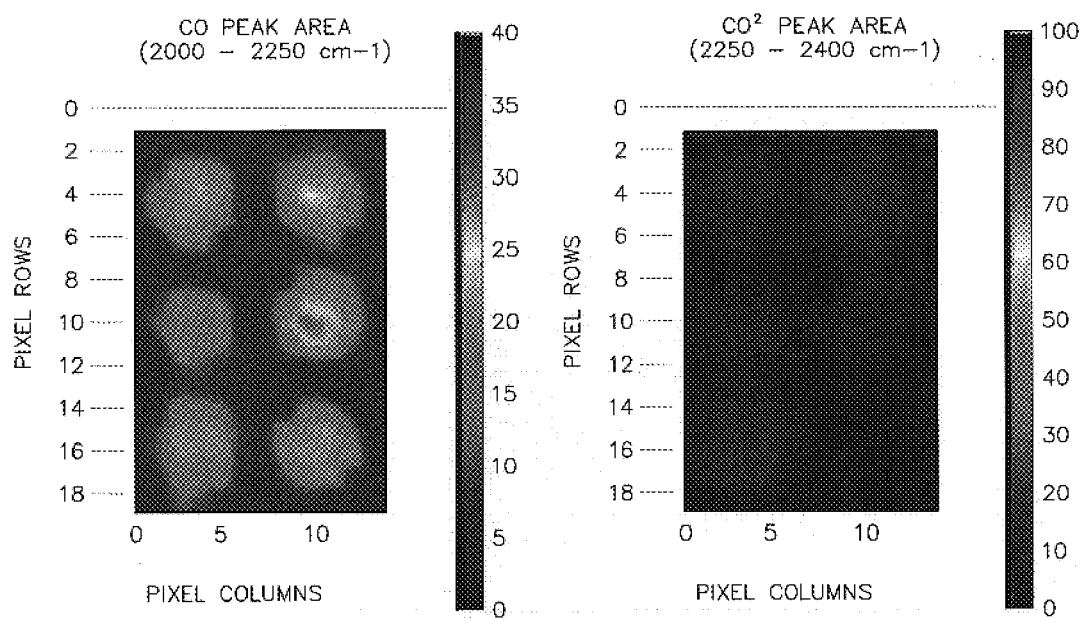
Figure 8D:
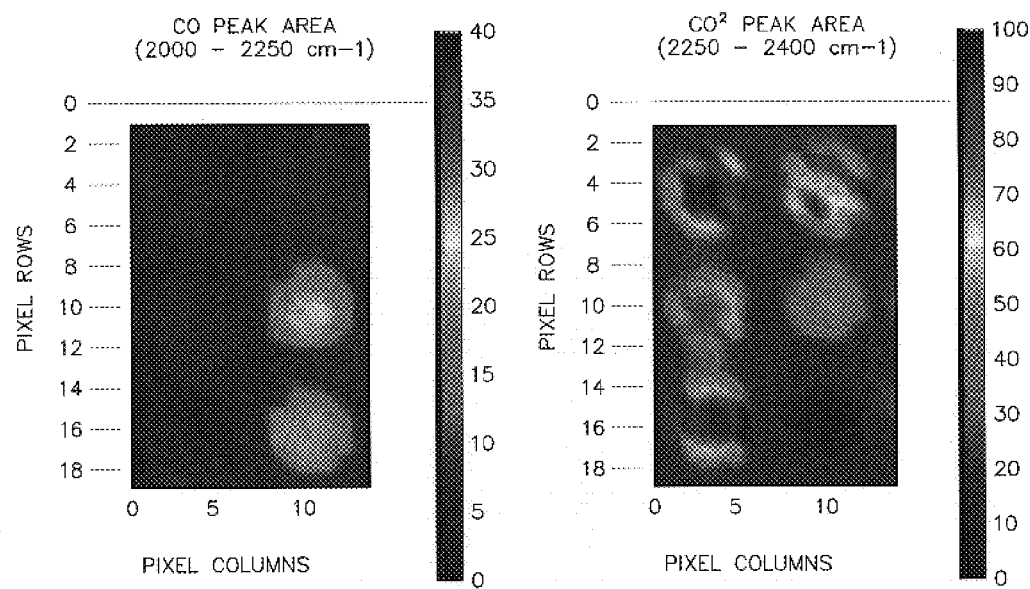
Figure 8E:
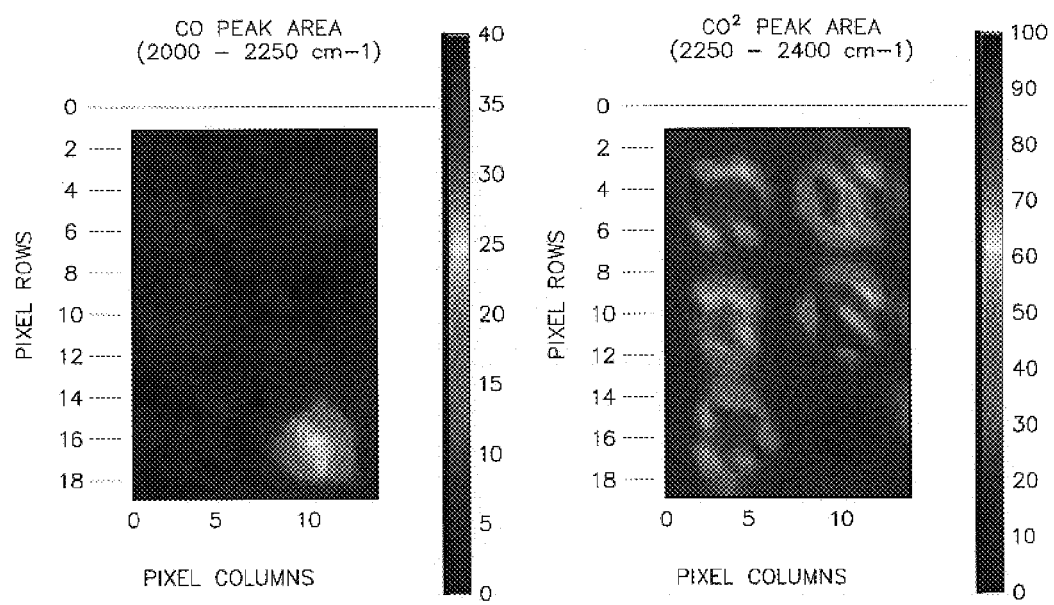
Figure 9:
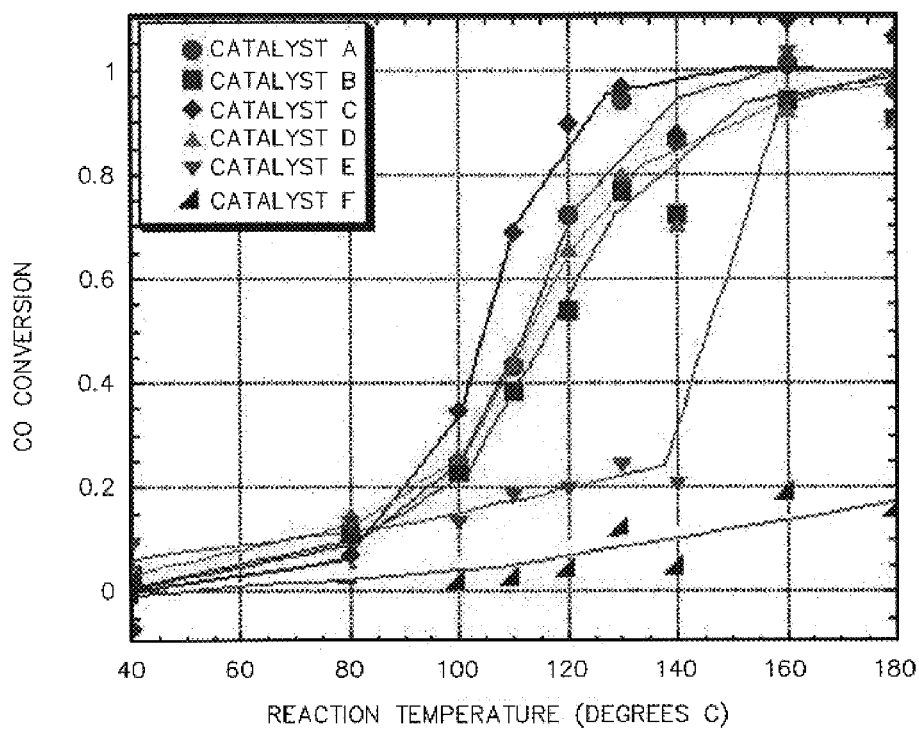
FIG. 9 is a graphical representation of lightoff curve data for six different catalysts derived from the experimental data shown in FIGS. 8A through 8E, as described in Example 2.

FIG. 8A shows the spatial configuration of the reaction vessels and corresponding spatial configuration of the detection cells/detection images for the six candidate catalyst compositions, designated as Catalyst A through Catalyst F. FIGS. 8B through 8E show the experimental results, reported as a set of images representing the integrated peak areas for carbon monoxide (CO) [left set of six images] and for carbon dioxide ($CO_2$) [right set of images] for experiments conducted at a reaction temperature of 40° C. (FIG. 8B), 100° C. (FIG. 8C), 140° C. (FIG. 8D) and 180° C. (FIG. 8E). As seen qualitatively, by comparing the left and right sets of images for each of these figures, relatively little CO is converted to $CO_2$ at 40° C. by any of the Catalysts A through F. At 100° C., however, each of Catalysts A through D are converting (oxidizing) a substantial portion of the CO to $CO_2$ (with Catalyst C being particularly active), whereas the commercial standard Catalyst E is not active. As temperature is further increased to 140° C., each of Catalysts A through D catalyze a high conversion of CO to $CO_2$, and the commercial standard Catalyst E begins to become active, but with relatively lower conversion. Finally, at 180° C., each of Catalysts A through D as well as commercial standard Catalyst E are highly active for this oxidation reaction. As expected, the blank catalyst composition, designated as Catalyst F, is not active for this reaction at any of the investigated temperatures. A more quantitative illustration of these results is shown in FIG. 9, which is a graphical plot of the CO conversion (calculated from the CO peak areas) versus reaction temperature for each of Catalysts A through F. Consistent with the FIGS. 8B through 8E, each of Catalysts A through D have a lower light-off temperature than the commercial standard Catalyst E. These data demonstrate that the parallel FTIR detection system can be effective for analyzing reaction products and unreacted reactants to evaluate heterogenous catalysts.

CONCLUSIONS

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. That is, it should be understood that the invention is not limited to the exact embodiment or construction which has been illustrated and described but that various changes may be made without departing from the spirit and the scope of the invention.

We claim:

1. An apparatus for simultaneously evaluating flow reactions comprising a parallel infrared detection system for simultaneously analyzing at least two flowing fluid samples, comprising:

a parallel flow reactor comprising two or more reactors, each of the two or more reactors comprising a reaction cavity for carrying out a chemical reaction, an inlet port in fluid communication with the reaction cavity for providing a feed stream comprising one or more reactants to the reaction cavity, and an outlet port in fluid communication with the reaction cavity for discharging an effluent stream comprising one or more reaction products, and a fluid distribution system comprising a feed distribution subsystem for simultaneously supplying the feed stream to the inlet port of each of the two or more reactors, and an effluent distribution subsystem for discharging the effluent stream from the outlet port of each of the two or more reactors, the parallel infrared detection system comprising (a) at least two detection cells, each of the at least two detection cells comprising (i) a detection cavity having one or more infrared reflective surfaces for reflecting infrared radiation, (ii) an inlet port for receiving one of the at least two samples into the detection cavity, and (iii) an outlet port for discharging the sample from the detection cavity;

(b) one or more infrared radiation sources for simultaneously irradiating each of the at least two samples with infrared radiation in the detection cavity of their respective detection cells, the one or more infrared radiation sources and the one or more infrared reflective surfaces being configured such that infrared radiation reflects off of the one or more infrared reflective surfaces within the detection cavity of each of the detection cells; and (c) a detector configured for simultaneously detecting reflected infrared radiation from each of the detection cells over time for analysis of the samples, wherein the effluent distribution subsystem of the parallel flow reactor is configured such that at least a portion of the discharged effluent steam of one of the two or more reactors is provided as a flowing fluid sample to the inlet port of a respective one of the detection cells.

2. An apparatus as in claim 1 wherein the one or more reflective surfaces are formed of a broadband IR reflective material.

3. An apparatus as in claim 2 wherein the reflective material is selected from gold, silver or a metal halide.

4. An apparatus as in claim 1 wherein the at least two detection cells includes at least four detection cells.

5. An apparatus as in claim 4 wherein the at least four detection cells includes at least 16 detection cells.

6. An apparatus as in claim 1 wherein the detection system has a detection limit below about 1000 ppm.

7. An apparatus as in claim 1 wherein the detection system has a detection limit below about 100 ppm.

8. An apparatus as in claim 1 wherein the one or more infrared reflective surfaces include a reflective end surface.

9. An apparatus as in claim 8 wherein the reflective end surface is proximate to the inlet port.

10. An apparatus as in claim 1 wherein the one or more infrared reflective surfaces include a waveguide.

11. An apparatus as in claim 1 wherein the one or more infrared reflective surfaces include a waveguide and a reflective end surface.

12. An apparatus comprising a parallel infrared detection system for simultaneously analyzing at least two flowing fluid samples, the detection system comprising
   (a) at least two detection cells, each of the at least two detection cells comprising (i) an elongated detection cavity comprising a first end, a second end defined by an infrared-transparent window, and an elongated side surface between the first end and the second end, the elongated side surface being effective for guiding an infrared wave of radiation along the elongated cavity, (ii) an inlet port for receiving one of the at least two samples into the detection cavity, and (iii) an outlet port for discharging the sample from the detection cavity,
   (b) one or more infrared radiation sources for simultaneously irradiating each of the at least two samples with infrared radiation in the detection cavity of their respective detection cells, the one or more infrared radiation sources being configured to provide Incident infrared radiation through the infrared-transparent window of each detection cavity such that the incident infrared radiation interacts with the sample in the respective detection cavity, and
   (c) a detector configured for simultaneously detecting infrared radiation from each of the detection cells over time for analysis of the samples, wherein the at least two detection cells are configured in relative relation to each other to have a first-end pitch defined by the center-to-center distance between adjacent detection cavities at the first end thereof, and a second-end pitch defined by the center-to-center distance between adjacent detection cavities at the second end thereof, the first-end pitch of the at least two detection cells being greater than the second-end pitch of the at least two detection cells.

13. The apparatus of claim 12 wherein for each of the at least two detection cells, at least a portion of the elongated detection cavity is non-linear, the non-linear portion of the elongated detection cavity comprising a non-linear elongated side surface.

14. The apparatus of claim 12 wherein for each of the at least two detection cells, the outlet port is positioned proximate to the infrared transparent window.

15. The apparatus of claim 12 wherein for each of the at least two detection cells, the outlet port is defined by a spaced relationship between an open end of the elongated side surface and the infrared transparent window.

16. An apparatus comprising a parallel infrared detection system for simultaneously analyzing at least two flowing fluid samples, the detection system comprising
   (a) at least two detection cells, each of the at least two detection cells comprising (i) an elongated detection cavity comprising a first end, a second end defined by an infrared-transparent window, and an elongated side surface between the first end and the second end, the elongated side surface being effective for guiding an infrared wave of radiation along the elongated cavity, (ii) an inlet port for receiving one of the at least two samples into the detection cavity, and (iii) an outlet port for discharging the sample from the detection cavity,
   (b) one or more infrared radiation sources for simultaneously irradiating each of the at least two samples with infrared radiation in the detection cavity of their respective detection cells, the one or more infrared radiation sources being configured to provide incident infrared radiation trough the infrared-transparent window of each detection cavity such that the incident infrared radiation interacts with the sample in the respective detection cavity,
   (c) a detector configured for simultaneously detecting infrared radiation from each of the detection cells over time for analysis of the samples, and a pressure chamber in fluid communication with the outlet port of each of the at least two detection cells.

17. The apparatus of claim 16 wherein the pressure chamber is adapted for operating conditions comprising a pressure of at least about 100 psig and for a temperature of at least about 100° C.

18. The apparatus of claim 16 further comprising a pressure regulator for regulating the pressure in the pressure chamber.

19. The apparatus of claim 16 wherein the pressure chamber includes a sweep system comprising a sweep gas source, an inlet port in fluid communication with the sweep gas source for admitting the sweep gas into the pressure chamber, an outlet port for discharging the sweep gas out of the pressure chamber, and a pressure regulator for regulating the pressure in the pressure chamber.

20. The apparatus of claim 12 wherein the detector comprises a focal plane array comprising at least eight pixels, the focal plane ray and the detection cells being configured, such that (i) for each of the at least two detection cells, infrared radiation is received from the detection cell into at least four pixels of the focal plane array, and (ii) at least about 50% of the total number of pixels of the focal plane array receive reflected infrared radiation from a detection cell.

21. The apparatus of claim 12 wherein the first end of the elongated detection cavity is defined by an infrared-reflective end surface for reflecting infrared radiation.

22. The apparatus of claim 12 wherein the first end of the elongated detection cavity is defined by an infrared-reflective end surface for reflecting infrared radiation, and the detector is configured for simultaneously receiving infrared radiation from each of the detection cells through the infrared transparent window.

23. An apparatus comprising a parallel infrared detection system for simultaneously analyzing at least two flowing fluid samples, the detection system comprising
   (a) at least two detection cells, each of the at least two detection cells comprising (i) an elongated detection cavity comprising a first end defined by an infrared-reflective end surface for reflecting infrared radiation, a second end defined by an infrared-transparent window, and an elongated side surface between the first end and the second end, the elongated side surface being defined at least partially by a capillary waveguide, at least a portion of the elongated detection cavity being non-linear, (ii) an inlet port for receiving one of the at least two samples into the detection cavity, and (iii) an outlet port for discharging the sample from the detection cavity, the at least two detection cells being configured in relative relation to each other to have a first-end pitch defined by the center-to-center distance between adjacent detection cavities at the first end thereof, and a second-end pitch defined by the center-to-center distance between adjacent detection cavities at the second end thereof, the first-end pitch of the at least two detection cells being greater than the second-end pitch of the at least two detection cells (b) one or more infrared radiation sources for simultaneously irradiating each of the at least two samples with infrared radiation in the detection cavity of their respective detection cells, the one or more infrared radiation sources being configured to provide incident infrared radiation through the infrared-transparent window of each detection cavity such that the incident infrared radiation interacts with the sample in the respective detection cavity, and (c) a detector comprising a focal plane array and being configured for simultaneously detecting infrared radiation from each of the detection cells over time for analysis of the samples, the focal plane array and the detection cells being configured, such that (i) for each of the at least two detection cells, infrared radiation is received from the detection cell into at least four pixels of the focal plane array, and (ii) at least about 50% of the total number of pixels of the focal plane array receive reflected infrared radiation from a detection cell.

24. An apparatus, for simultaneously evaluating flow reactions comprising a parallel infrared detection system for simultaneously analyzing at least two flowing fluid samples, comprising a parallel flow reactor comprising two or more reactors, each of the two or more reactors comprising a reaction cavity for carrying out a chemical reaction, an inlet port in fluid communication with the reaction cavity for providing a feed stream comprising one or more reactants to the reaction cavity, and an outlet port in fluid communication with the reaction cavity for discharging an effluent stream comprising one or more reaction products, and a fluid distribution system comprising a feed distribution subsystem for simultaneously supplying the feed stream to the inlet port of each of the two or more reactors, and an effluent distribution subsystem for discharging the effluent stream from the outlet port of each of the two or more reactors, the parallel infrared detection system comprising (a) at least two detection cells, each of the at least two detection cells comprising (i) an elongated detection cavity comprising a first end, a second end defined by an infrared-transparent window, and an elongated side surface between the first end and the second end, (ii) an inlet port for receiving one of the at least two samples into the detection cavity, and (iii) an outlet port for discharging the sample from the detection cavity, (b) one or more infrared radiation sources for simultaneously irradiating each of the at least two samples with infrared radiation in the detection cavity of their respective detection cells, the one or more infrared radiation sources being configured to provide incident infrared radiation through the infrared-transparent window of each detection cavity such that the incident infrared radiation interacts with the sample in the respective detection cavity; and (c) one or more detectors configured for simultaneously detecting infrared radiation from each of the detection cells over time for analysis of the samples;

wherein each of the detection cavities, the one or more infrared sources, the infrared-transparent window of each detection cavity, and the one or more detectors are configured such that the detection system has a detection limit below about 100 ppm, and wherein the effluent distribution subsystem of the parallel flow reactor is configured such that at least a portion of the discharged effluent stream of one of the two or more reactors is provided as a flowing fluid sample to the inlet port of a respective one of the detection cells.

25. An apparatus as in any of claims 1, 12, 16, 23 or 24 further comprising a processor for performing Fourier transform infrared analysis on the reflected infrared radiation or images thereof.

26. An apparatus as in claim 25 wherein the processor performs the Fourier transform infrared analysis simultaneously for the at least two samples.

27. A method for simultaneously analyzing at least two flowing fluid samples using parallel infrared detection, the method comprising:

providing a parallel flow reactor comprising two or more reactors, each of the two or more reactors comprising a reaction cavity, an inlet port in fluid communication with the reaction cavity and an outlet port in fluid communication with the reaction cavity;

providing a fluid distribution system comprising a feed distribution subsystem and an effluent distribution subsystem;

providing at least two detection cells, each of the at least two detection cells comprising (i) a detection cavity having one or more infrared reflective surfaces for reflecting infrared radiation, (ii) an inlet port for receiving one of the at least two samples into the detection cavity, and (iii) an outlet port for discharging the sample from the detection cavity;

simultaneously feeding a reactant stream comprising one or more reactants through the inlet port of each of the two or more reactors to the reaction cavity of each of the two or more reactors, simultaneously contacting the one or more reactants with a catalyst in the reaction cavity under reaction conditions to form one or more reaction products;

discharging the one or more reaction products from the reaction cavity of each of the reactors as an effluent stream through the outlet port of each of the reaction cavities to the effluent distribution subsystem of the fluid distribution system;

providing at least a portion of the discharged effluent stream from each of the reactors to the inlet port of each of the detection cells as the at least two fluid samples;

simultaneously flowing the at least two fluid samples respectively through the inlet port of each of the detection cells into the detection cavity;

simultaneously directing infrared radiation through an infrared transparent window into the detection cavity of each of the detection cells such that the infrared radiation reflects off of the one or more infrared reflective surfaces within the detection cavity of each of the detection cells and respectively interacts with each of the at least two samples for simultaneously irradiating the at least two samples with reflected infrared radiation;

simultaneously detecting the reflected infrared radiation from each of the detection cells over time for analysis of the samples; and simultaneously flowing the at least two fluid samples respectively out of the detection cavity of each of the detection cells through the outlet port of each of the detection cells.

28. A method as in claim 27 wherein the one or more reflective surfaces are formed of a broadband IR reflective material.

29. A method as in claim 27 wherein the one or more reflective surfaces are formed from a material selected from gold, silver or a metal halide.

30. A method as in claim 27 wherein the at least two detection cells includes at least four detection cells.

31. A method as in claim 27 wherein the at least two detection cells includes at least 16 detection cells.

32. A method as in claim 27 wherein the detection system has a detection limit below about 1000 ppm.

33. A method as in claim 27 wherein the detection system has a detection limit below about 100 ppm.

34. A method as in claim 27 wherein the one or more infrared reflective surfaces includes a reflective end surface that is proximate to the inlet port.

35. A method as in claim 27 wherein the at least two samples are reaction products of different reactions.

36. A method of performing parallel infrared detection for simultaneously analyzing at least two flowing fluid samples, the method comprising:
providing at least two detection cells, each of the at least two detection cells comprising (i) an elongated detection cavity comprising a first end, a second end defined by an infrared-transparent window, and an elongated side surface between the first end and the second end, (ii) an inlet port for receiving one of the at least two samples into the detection cavity, and (iii) an outlet port for discharging the sample from the detection cavity;
flowing the at least two fluid samples respectively through the inlet port of each of the detection cells into the detection cavity;
directing infrared radiation through an infrared transparent window into the detection cavity of each of the detection cells such that the elongated side surface reflects and guides the infrared radiation along the elongated cavity to respectively interact with each of the at least two samples for simultaneously irradiating the at least two samples with reflected infrared radiation;
detecting the reflected infrared radiation from each of the at least two detection cells over time for analysis of the samples; and
flowing the at least two fluid samples respectively out of the detection cavity of each of the at least two detection cells via the outlet port of each of the at least two detection cells, wherein the at least two detection cells are configured in relative relation to each other to have a first-end pitch defined by the center-to-center distance between adjacent detection cavities at the first end thereof, and a second-end pitch defined by the center-to-center distance between adjacent detection cavities at the second end thereof, the first-end pitch of the at least two detection cells being greater than the second-end pitch of the at least two detection cells.

37. The method of claim 36 wherein for each of the at least two detection cells, at least a portion of the elongated detection cavity is non-linear, the non-linear portion of the elongated detection cavity comprising a non-linear elongated side surface.

38. The method of claim 36 wherein for each of the at least two detection cells, the outlet port is positioned proximate to the infrared transparent window.

39. The method of claim 36 wherein for each of the at least two detection cells, the outlet port is defined by a spaced relationship between an open end of the elongated side surface and the infrared transparent window.

40. A The method of claim 36 wherein the at least two fluid samples flow out of the detection cavity into a common pressure chamber in fluid communication with the outlet port of each of the at least two detection cells.

41. The method of claim 40 wherein the pressure chamber is adapted for operating conditions comprising a pressure of at least about 100 psig and for a temperature of at least about 100° C.

42. The method of claim 40 further comprising regulating the pressure in the pressure chamber.

43. The method of claim 40 further comprising sweeping the pressure chamber with a sweep gas to reduce cross-contamination between fluid samples in adjacent detection cells.

44. The method of claim 36 wherein the detector comprises a focal plane array comprising at least eight pixels, and (i) for each of the at least two detection cells, the reflected infrared radiation from the detection cell is received into at least four pixels of the focal plane array, and (ii) at least about 50% of the total number of pixels of the focal plane array receive reflected infrared radiation from a detection cell.

45. The method of claim 36 wherein the first end of the elongated detection cavity is defined by an infrared-reflective end surface for reflecting infrared radiation.

46. The method of claim 36 wherein the first end of the elongated detection cavity is defined by an infrared-reflective end surface for reflecting infrared radiation, and the detector is configured for simultaneously receiving infrared radiation from each of the detection cells through the infrared transparent window.

47. A method of performing parallel infrared detection for simultaneously analyzing at least two flowing fluid samples, the method comprising:
providing a parallel flow reactor comprising two or more reactors, each of the two or more reactors comprising a reaction cavity, an inlet port in fluid communication with the reaction cavity and an outlet port in fluid communication with the reaction cavity;
providing a fluid distribution system comprising a feed distribution subsystem and an effluent distribution subsystem;
providing at least two detection cells, each of the at least two detection cells comprising (i) a detection cavity having one or more infrared reflective surfaces for reflecting infrared radiation, (ii) an inlet port for receiving one of the at least two samples into the detection cavity, and (iii) an outlet port for discharging the sample from the detection cavity;
simultaneously feeding a reactant stream comprising one or more reactants through the inlet port of each of the two or more reactors to the reaction cavity of each of the two or more reactors,
simultaneously contacting the one or more reactants with a catalyst in the reaction cavity under reaction conditions to form one or more reaction products;

discharging the one or more reaction products from the reaction cavity of each of the reactors as an effluent stream trough the outlet port of each of the reaction cavities to the effluent distribution subsystem of the fluid distribution system;

providing at least a portion of the discharged effluent stream from each of the reactors to the inlet port of each of the detection cells as the at least two fluid samples;

flowing the at least two fluid samples respectively through the inlet port of each of the detection cells into the detection cavity;

directing infrared radiation through an infrared transparent window into the detection cavity of each of the detection cells such that the infrared radiation reflects off of the one or more infrared reflective surfaces within the detection cavity of each of the detection cells and respectively interacts with each of the at least two samples for simultaneously irradiating the at least two samples with reflected infrared radiation;

detecting the reflected infrared radiation from each of the detection cells over time with a detection limit below about 100 ppm for one or more components of each of the samples; and flowing the at least two fluid samples respectively out of the detection cavity of each of the detection cells via the outlet port of each of the detection cells.

48. A method as in any of claims 27, 36, or 47 further comprising, performing Fourier transform infrared analysis upon the reflected infrared radiation or images thereof.

49. A method of claim 48 wherein the step of performing Fourier transform infrared analysis is carried out simultaneously for the at least two samples.

* * * * *

UNITED STATES PATENT AND TRADEMARK OFFICE
CERTIFICATE OF CORRECTION

PATENT NO. : 7,255,474 B2  Page 1 of 1
APPLICATION NO. : 10/900612
DATED : August 14, 2007
INVENTOR(S) : Cong et al.

It is certified that error appears in the above-identified patent and that said Letters Patent is hereby corrected as shown below:

Column 33, claim 12, line 35:   "Incident" should read -- incident --.

Column 34, claim 16, line 16:   "trough" should read -- through --.

Column 39, claim 47, line 3:    "trough" should read -- through --.

Signed and Sealed this

Ninth Day of September, 2008

JON W. DUDAS
*Director of the United States Patent and Trademark Office*